United States Patent
Rangel-Aldao et al.

(10) Patent No.: US 6,468,567 B1
(45) Date of Patent: Oct. 22, 2002

(54) MALT BEVERAGE HAVING STABILIZED FLAVOR AND METHODS OF PRODUCTION THEREOF

(75) Inventors: Rafael Rangel-Aldao, Caracas (VE); Adriana Bravo, Caracas (VE); Beatriz Sanchez, Miranda (VE); Ivan Galindo-Castro, Caracas (VE)

(73) Assignee: Cerveceria Polar, C.A., Caracas (VE)

( * ) Notice: Subject to any disclaimer, the term of this patent is extended or adjusted under 35 U.S.C. 154(b) by 0 days.

(21) Appl. No.: 09/665,313

(22) Filed: Sep. 19, 2000

Related U.S. Application Data

(62) Division of application No. 09/150,347, filed on Sep. 9, 1998, now Pat. No. 6,372,269.
(60) Provisional application No. 60/058,398, filed on Sep. 9, 1997.

(51) Int. Cl.[7] .................................................. A23C 9/12
(52) U.S. Cl. .............................. 426/62; 426/64; 439/93
(58) Field of Search ............................ 435/25, 189, 93; 426/62, 64

(56) References Cited

U.S. PATENT DOCUMENTS

| | | | |
|---|---|---|---|
| 4,110,480 A | 8/1978 | Pollock et al. | 426/436 |
| 4,387,162 A | 6/1983 | Aigle et al. | 435/172 |
| 4,414,334 A | 11/1983 | Hitzman | 435/262 |

(List continued on next page.)

FOREIGN PATENT DOCUMENTS

| | | |
|---|---|---|
| EP | 0 207 039 | 12/1986 |
| EP | 0 773 285 | 5/1997 |
| EP | 0 832 974 | 4/1998 |
| EP | 0 924 294 | 6/1999 |
| GB | 5673 | 2/1891 |
| JP | 2-46285 | 2/1990 |
| JP | 3-65173 | 3/1991 |

OTHER PUBLICATIONS

Abramovitz, A.S., and Massey, V., "Purification of Intact Old Yellow Enzyme Using an Affinity Matrix for the Sole Chromatographic Step," *J. Biol. Chem.* 251:5321–5326, American Society for Biochemistry and Molecular Biology, Inc., Baltimore, MD (1976).

(List continued on next page.)

*Primary Examiner*—Ponnathapu Achutamurthy
*Assistant Examiner*—Kathleen Kerr
(74) *Attorney, Agent, or Firm*—Sterne, Kessler, Goldstein & Fox P.L.L.C.

(57) ABSTRACT

The present invention is directed to a method for stabilizing the flavor of a fermented malt beverage, most particularly a beer, by the addition of one or more inhibitors, blockers, reducing agents or binding agents that inactivate one or more Maillard reaction intermediates that induce staling of the flavor of fermented malt beverages. In preferred such methods, the agents used are reductase enzymes, especially aldehyde reductases, carbonyl reductases, aldose reductases, oxoaldehyde reductases and most particularly oxidoreductases such as isozymes of Old Yellow Enzyme (OYE;EC 1.6.99.1) (e.g., OYE1 and OYE2 and OYE3). The invention is also directed to the fermented malt beverage prepared by such a method, and to the use during the brewing process of reductase enzymes from naturally occurring sources, including those produced by yeasts, to stabilize the flavor of the resulting beer product and to produce a beer having a stable flavor. The invention also relates to cells which have been specifically modified, selected, or genetically engineered to express or secrete a reductase enzyme which may be used during the brewing process to stabilize the flavor of the resulting beer product and to produce a beer having a stable flavor. The invention also provides fermented malt beverages having enhanced flavor stability produced by these methods.

20 Claims, 12 Drawing Sheets

U.S. PATENT DOCUMENTS

| | | | |
|---|---|---|---|
| 4,790,993 A | 12/1988 | Schedl et al. ................. | 426/13 |
| 4,867,990 A | 9/1989 | Suwa et al. ..................... | 426/8 |
| 4,911,936 A | 3/1990 | Kijima et al. ................. | 426/62 |
| 4,957,749 A | 9/1990 | Prieels et al. ................. | 426/10 |
| 5,010,007 A | 4/1991 | Prieels et al. ............... | 435/190 |
| 5,043,276 A | 8/1991 | Yamano et al. ............. | 435/161 |
| 5,055,401 A | 10/1991 | Liljeström et al. ........ | 435/172.3 |
| 5,298,264 A | 3/1994 | Edens et al. ................... | 426/8 |
| 5,460,836 A | 10/1995 | Ono et al. ..................... | 426/11 |
| 5,512,472 A | 4/1996 | Lai et al. ................. | 435/240.1 |

OTHER PUBLICATIONS

Baker, D.L., and Stollberg, H., "The Relation between Yeast Strain and Flavor Stability of Beer," *The Brewers Digest*, pp. 46–47, Siebel Publishing Co., Chicago, IL. (1959).

Bravo, A., et al., "Capillary electrophoresis for Studying Beer Aging," *IBTC Technical Consortium Meeting #35*, Salzburg, Austria, unpublished abstract of poster presentation (1993).

Bravo, A., et al., "Use of HPLC and CE to Detect Chemical Indices of Beer Aging," *IBTC Technical Consrtium Meeting #36*, Caracas, Venezuela, unpublished abstract of poster presentation (1994).

Collin, S., et al., "Yeast dehydrogenase activities in relation to carbonyl compounds removal from wort and beer," *Proc. Cong. Eur. Brew. Conv.* 23:409–416, IRL Press Limited, Oxford, England (1991).

Dalgliesh, C.E., "Flavour Stability," *Proc. Cong. Eur. Brew. Conv.* ($16^{th}$ Cong.):623–659, IRL Press Limited, Oxford, England (1977).

Debourg, A., et al., "The specific role and interaction of yeast enzymatic systems in the removal of flavour–potent wort carbonyls during fermentation," *EBC Congress*, pp. 437–444, IRL Press Limited, Oxford, England (1993).

Debourg, A., et al., "Wort Aldehyde Reduction Potential in Free and Immobilized Yeast Systems," *J. Am. Soc. Brew. Chem.* 52:100–106, American Society of Brewing Chemists, Inc., St. Paul, Minnesota (1994).

Greenhoff, K., and Wheeler, R.E., "Analysis of Beer Carbonyls at the Part Per Billion Level by Combined Liquid Chromatography and High Pressure Liquid Chromatography," *J. Inst. Brew.* 86:35–41, Heriott Watt University, Edinburgh, Scotland (1981).

Grönqvist, A., et al., "Carbonyl compounds during beer production and in beer," *Proc. Cong. Eur. Brew. Conv.* 24:421–428, IRL Press Limited, Oxford, England (1993).

Hansen, J., and Kielland–Brandt, M.C., "Inactivation of MET10 in brewer's yeast specifically increases $SO_2$ formation during beer production," *Nature Biotechnol.* 14:1587–1591, Nature Publishing Co., New York, NY (Nov. 1996).

Harayama, K., et al., "Evaluation by Multivariate Analysis of Off–flavor in Headspace Volatiles Formed during Storage of Beer," *Agric. Biol. Chem.* 55:393–398, Japan Society for Bioscience, Biotechnology, and Agrochemistry, Tokyo, Japan (1991).

Hashimoto, N., "Amino–Carbonyl Reaction During Wort Boiling in Relation to Flavor Stability of Beer," *MBAA Tech. Quarterly* 11:121–126, Master Brewers Association of the Americas, Wauwatosa, WI (1974).

Hashimoto, N., "Stale Flavor Derived from Higher Alcohols and Isohumulones in Beer," *Rept. Res. Lab. Kirin Brewery Co., Ltd.*, 19:1–8, Kirin Brewery Co., Ltd., Tokyo, Japan (1976).

Karplus, P.A., et al., "Structure–function relations for old yellow enzyme," *FASEB J.* 9:1518–1526, The Federation of American Societies for Experimental Biology, Bethesda, MD (1995).

Kronlöf, J., et al., "Main fermentation with immobilized yeast," *Proc. Cong. Eur. Brew. Conv.* 22:355–362, IRL Press, Oxford, England (1989).

Liang, Z.–Q., et al., "Aldose Reductase from Porcine Liver Metabolizing 3–Deoxyglucosone, a Maillard Reaction Intermediate," *Biosci. Biotech. Biochem.* 56:1074–1078, Japan Society for Bioscience, Biotechnology, and Agrochemistry, Tokyo, Japan (1992).

Lowry, O.H., et al., "Protein Measurement with the Folin Phenol Reagent," *J. Biol. Chem.* 193:265–275, American Society for Biochemistry and Molecular Biology, Inc., Baltimore, MD (1951).

Madani, N.D., et al., "*Candida albicans* estrogen–binding protein gene encodes an oxidoreductase that is inhibited by estradiol," *Proc. Natl. Acad. Sci. USA* 91:922–926, National Academy of Sciences of the USA, Washington, D.C. (1994).

Mathews, S., et al., "Chemical indices of food decomposition," *Trends Food Sci. & Technol.* 1:89–91, Elsevier Trends Journals, Cambridge, England (1990).

Meilgaard, M.C., "Flavor Chemistry of Beer: Part II: Flavor and Threshold of 239 Aroma Volatiles," *MBAA Tech. Quarterly* 12:151–168, Master Brewers Association of the Americas, Wauwatosa, WI (1975).

Miranda, M., et al., "Nucleotide Sequence and Chromosomal Localization of the Gene Encoding the Old Yellow Enzyme from *Kluyveromyces lactis*," *Yeast* 11:459–465, John Wiley, Chichester, NY (1995).

Miura, R., et al., "The Heterogeneity of Brewer's Yeast Old Yellow Enzyme," *J. Biochem.* 99:901–906, Japanese Biochemical Society, Tokyo, Japan (1986).

Murakami, H., et al., "Expression of Cloned Yeast NADPH–Cytochrome P450 Reductase Gene in *Saccharomyces cerevisiae*," *J. Biochem.* 108:859–865, Japanese Biochemical Society, Tokyo, Japan (1990).

Murata, K., et al., "Metabolism of 2–oxoaldehyde in yeasts. Purification and characterization of NADPH–dependent methylglyoxal–reducing enzyme from *Saccharomyces cerevisiae*," *Eur. J. Biochem.* 151:631–636, Blackwell Science Ltd., Berlin, Germany (1985).

Murata, K., et al., "2–Oxoaldehyde metabolism in microorganisms," *Can. J. Microbiol.* 35:423–431, National Research Council Of Canada, Ottowa, Canada (1989).

Narziβ, L., et al., "Technological Approach to Improve Flavour Stability," *MBAA Tech. Quarterly* 30:48–53, Master Brewers Association of the Americas, Wauwatosa, WI (1993).

Niino, Y.S., et al., "A New Old Yellow Enzyme of *Saccharomyces cerevisiae*," *J. Biol. Chem.* 270:1983–1991, American Society for Biochemistry and Molecular Biology, Inc., Baltimore, MD (1995).

Peppard, T.L., and Halsey, S.A., "Malt Flavour—Transformation of Carbonyl Compounds by Yeast During Fermentation," *J. Inst. Brew.* 87:386–390, Heriott Watt University, Edinburgh, Scotland (1981).

Rangel–Aldao, R., "South American starter cultures," *Nature Biotechnol.* *14*:951–952, Nature Publishing Co., New York, NY (Aug. 1996).

Rangel–Aldao, R., "Biotechnology for a better beer?" *Nature Biotechnol.* *14*:1540–1541, Nature Publishing Co., New York, NY (Nov. 1996).

Saito, K., et al., "The Cloning and Expression of a Gene Encoding Old Yellow Enzyme from *Saccharomyces carlsbergensis*," *J. Biol. Chem.* *266*:20720–20724, American Society for Biochemistry and Molecular Biology, Inc., Baltimore, MD (1991).

Stott, K., et al., "Old Yellow Enzyme," *J. Biol. Chem.* *268*:6097–6106, American Society for Biochemistry and Molecular Biology, Inc., Baltimore, MD (1993).

Strating, J., and Drost, B.W., "Limits of Beer Flavour Analysis," *Dev. Food Sci.* *17*:109–121, Elsevier, New York, NY (1987).

Watson, J.D., et al., "Using Yeast to Study Eukaryotic Gene Function," in *Recombinant DNA, Second Edition*, Scientific American Books, New York, NY, pp. 235–253 (1992).

Weber, K., and Osborn, M., "The Reliability of Molecular Weight Determinations by Dodecyl Sulfate–Polyacrylamide Gel Electrophoresis," *J. Biol. Chem.* *244*:4406–4412, American Society for Biochemistry and Molecular Biology, Inc., Baltimore, MD (1969).

Zhao, X., et al., "Oestrogen–binding protein in *Candida albicans*: antibody development and cellular localization by electron immunocytochemistry," *Microbiology* *141*:2685–2692, Society for General Microbiology, Reading, UK (1995).

Dialog File 351 (Derwent World Patents Index), English language abstract for European Patent Office Publication No. EP 0 207 039 (Document AM1), WPI Accession No. 86–341313/198652.

Japanese Patent Office, Patent Abstracts of Japan, English language abstract for Japanese Patent Office Publication No. JP 2–46285 (Document AN1).

Japanese Patent Office, Patent Abstracts of Japan, English language abstract for Japanese Patent Office Publication No. JP 3–65173 (Document AO1).-

| Substrate | Activity (nmol/min/mg) | |
|---|---|---|
| | Reductase 1 | Reductase 2 |
| Pyridine-3-aldehyde | 111.5 | 0.0 |
| D-glucoronate | 7.0 | 182.1 |
| Acetaldehyde | 585.8 | 41.9 |
| Methylglyoxal | 331.6 | 230.3 |
| D-glucose | 23.1 | 0.0 |
| D-galactose | 12.1 | 0.0 |
| D-xylose | 34.2 | 0.0 |
| Metyrapone | 329.6 | 383.0 |
| 2,3-butanodione | 238.1 | 189.5 |
| 2,3-pentanodione | 20.1 | 0.0 |
| 3-deoxyglucosone | 190.9 | 115.1 |
| Pyruvate | 9.0 | 0.0 |

FIG. 10

MALT BEVERAGE HAVING STABILIZED FLAVOR AND METHODS OF PRODUCTION THEREOF

CROSS REFERENCE TO RELATED APPLICATION

The present application is a divisional of U.S. application Ser. No. 09/150,347, filed Sep. 9, 1998, now U.S. Pat. No. 6,372,269 which claims the benefit of U.S. Provisional Application No. 60/058,398, filed Sep. 9, 1997, the disclosures of which is incorporated herein by reference in their entireties.

BACKGROUND OF THE INVENTION

1. Field of the Invention

The present invention is in the fields of biotechnology and food/beverage manufacturing. The invention relates to the production of malt beverages, and more particularly to the production of malt beverages having improved flavor-stability. In particular, the invention relates to methods and compositions for improving the flavor stability of fermented malt beverages such as beer, and to malt beverages produced by these methods.

2. Related Art

The Brewing Process

Overview. In the production of fermented malt beverages such as beer, a warm water extract of barley malt, with or without other unmalted grains such as rice or corn, is boiled with hops, cooled and then subjected to the fermentative action of yeast. The warm water used to extract the malt allows the action of several enzymes in the malt to hydrolyze the starch in the barley (and in the corn or rice) to fermentable sugar, which is acted on by the yeast to produce the alcohol in the fermented malt beverage.

Malting. Barley malt is steeped with water to produce steeped out barley which is germinated at a fairly low temperature. Germination is carried out with daily mixing and water addition as needed to maintain the moisture content at about 43%. The resulting green malt contains a high content of beer flavor precursors, beer flavor components, and coloring agents. After germination is complete, the green malt is heated at a high moisture content to generate beer flavor precursors, beer flavor components and also to reduce amylolytic enzyme activity. After heating, the malt is dried to a moisture content of 3.5–5.5% and a soluble protein content of 6.5–8%. The dried malt can then be mashed to produce a wort which is boiled with hops, cooled, pitched with brewers yeast, and processed by conventional brewing processes and in conventional brewing equipment.

Mashing. The malt, which may actually be a blend of malts (i.e., standard brewer's malt, high color, low amylase malt, etc.), is ground and mixed with 2.5 to 4 times its weight of warm water in large tubs and mashed at 35–40° C. for 5 to 15 minutes until it forms a thick malt mash. The mash is then permitted to rest for 45–90 minutes without stirring, then heated in steps to 70–73° C. while stirring, with time allowed at each step for the various enzymes to convert the starches into fermentable sugars. Following heating, the mash is held for 15–30 minutes, the temperature is raised to 75° C., and the mash is transferred to the lauter unit.

If rice and corn adjuncts are to be used, they are separately cooked and a cooker mash is obtained. Production of the cooker mash involves the use of adjuncts along with a 10%–30% portion of the malt (or the addition of commercial enzymes) in order to convert raw starch into fermentable sugars. The adjuncts and the malt portion are gradually brought to boiling and held there until the products are completely gelatinized. During the final stages of mashing (at the higher temperatures), the cooker mash and the malt mash are combined.

Mashing serves a three-fold purpose. First, it brings into solution those substances of malt (and adjuncts) which are readily soluble in warm water. Second, it permits malt enzymes to act on insoluble substances and render them soluble. Third, it provides a far-reaching enzymatic degradation of starches, proteins and gums into products of smaller size and lower molecular weight.

Lautering and Sparging. Lautering consists of the removal of the liquid, now termed the "wort," from the insoluble husks or "spent grains." Lautering begins upon termination of the mashing process, whereby the finished mash is transferred to a lautering tub. There it is allowed to rest for about ten to thirty minutes during which time the spent grains settle to the bottom. The lautering tub is equipped with a false bottom containing numerous perforations and an outlet leading to the true bottom of the tub. The mash is then allowed to settle for 10–20 minutes and run-off begun. The wort is recycled until reasonably clear. The clear wort is then pumped into a brewing kettle. Hot water is run through the spent grains to rinse out, or sparge, any remaining wort.

The lauter temperature is about 72–77° C. for both the bath and sparge water. The amount of sparge water used is about 50–75% of the amount of brewing water.

Boiling and Hopping of Wort: Primary Fermentation. The wort is boiled vigorously for one to two and one-half hours in the brew kettle. Hops (or extracts thereof) may be added at various stages of the boiling process, depending on the nature of the final product that is sought.

Wort boiling serves a number of objectives, including (1) concentration of the sparged wort, (2) complete inactivation of enzymes that may have survived the final mashing process, (3) coagulation and precipitation of high-molecular weight proteins and solids (termed "kettle break" or "hot break"), (4) extraction of desirable hop constituents, and (5) sterilization of the wort.

Cooling, Fermentation and Storage: Maturation. After boiling, the wort is strained to remove the solids, or "trub," and the wort is then cooled to a temperature of about 12–16° C.

Fermentation is initiated when the wort is pitched with the proper amount of a pure brewer's yeast culture (typically about 0.7–1.5 lb/bbl). After 24 hours, fermentation is established and proceeds at an accelerated rate. Fermentation typically proceeds for about 7 to 10 days. During this period, the wort temperature must be controlled, since the fermentation process causes the temperature of the wort to rise. Once the yeast has metabolized all the fermentable ingredients in the wort, it settles to the bottom and is subsequently recovered and recycled for use in pitching other brews. As the fermentation process comes to a conclusion, the temperature of the wort begins to drop. The fermented wort (termed "green beer") is drawn off for storage in a cold room tank, or "ruh," where, its temperature is lowered to about 0–5° C.

Processing and Packaging. The "ruh" beer may be allowed to remain in the ruh tank for completion of the maturation process, or it may be transferred into a separate maturation tank upon further settling of any remaining yeast and other solids. Depending on the particular brewery, the beer is allowed to age from about 14 days to about 3 months. During this period, the beer clarifies and its flavor develops. Upon maturation, the beer generally is filtered to remove the yeasts and other solids.

The beer can undergo a single- or a double-pass filtration process. The double-pass filtration consists of two steps: a primary (coarse) filtration, and a secondary (fine) filtration. Filtered beer is subsequently stored in a finishing tank.

To prepare the beer for consumption, it is carbonated to a specified level. Then, depending on the form of packaging, the beer may be pasteurized. (In the case of the cold-filtered "draft" beers, a microfiltration system is used to remove contaminants, thereby obviating the pasteurization step.) Beer packaged in cans and bottles is usually pasteurized, while beer packaged in kegs (and sometimes bottles) remains unpasteurized. After final processing of the packaged product (e.g. labeling, etc.), the beer is ready for shipment to the consumer.

Other conventional processing steps well known to those skilled in the art may be used instead of, or in addition to, the above-disclosed general brewing methods. For example, the fermented wort can be diluted with water to produce a low calorie (40 or fewer calories per 12 ounces), non-alcoholic malt beverage (less than 0.5 volume percent alcohol) that closely simulates conventional beer flavor, taste and mouthfeel.

The Attributes of Fermented Malt Beverages

Malt beverages, especially beer, possess attributes readily discernable by the consumer. These attributes include foam, flavor and clarity. Of these, flavor is ultimately the most important characteristic to the consumer.

Flavor (purity) and after-taste (refreshing feeling) are typically measured within the industry as having one of the following five grades:

1: Taste is not very clean and after-taste has no refreshing feeling.
2: Taste is not clean and after-taste has almost no refreshing feeling.
3: Usual.
4: Taste is clean and after-taste has refreshing feeling.
5: Taste is very clean and after-taste has very refreshing feeling.

Flavor stability is typically evaluated in the stored packaged product (usually at a storage temperature of 28° C. for 15 days) as having one of the following five grades:

1: Significantly staled.
2: Staled.
3: Usual.
4: Fresh.
5: Very fresh.

In addition, an increasing number of consumers desire an all-natural beer product which demonstrates the above qualifies yet is entirely free of artificial additives or supplements.

It is known in the art that the malted barley may be replaced in whole or in part by a so called "brewing adjunct." Suitable brewing adjuncts include maize, rice, sugar and various syrups. A brewing adjunct used in the production of a wort, such as maize, is usually crushed and a mash formed separately from the malt mash by adding enzymes. Prehydrolyzed products can be mixed with the malt mash, and syrups can be added to the wort at the time the wort is boiled as described above. The use of brewing adjuncts needs to be carefully controlled in order to produce beer of acceptable taste and color. The use of adjuncts made from maize, rice and other grains expands the brewing ingredients beyond the traditional ones listed above. Such an approach is, however, not possible in certain countries—in Germany, for example, the Beer Purity Laws enacted in 1516 (the "Reinheitsgeböt") which limit brewing ingredients to barley malt, water, hops and yeast, are still followed.

Compounds added to the wort mixture prior to the primary fermentation step are termed "processing aids." On the other hand, compounds added to the wort mixture after the primary fermentation step are termed "additives." The difference between the two is significant because the use of additives is regulated, whereas the use of processing aids is not.

Flavor

As noted above, flavor is a key factor in the quality of a malt beverage such as beer. It is important that a beer retains its original, fresh flavor and character during distribution and storage. Thus, off-flavors are a great problem for beer manufacturers and distributors. The lightstruck flavor is a well-known off-flavor formed during the storage of bottled beer, as is the off-flavor caused by contamination with microorganisms. Other off-flavors that are produced during storage are expressed as papery, cardboard-like, oxidized, or in general, stale. At room temperature, the stale flavor in canned or bottled beer begins to develop shortly after packaging, and gradually and continuously increases to the extent that most American manufacturers of beer recall their product from the market if it is more than about 4 months from the packaging date. Although the oxygen in a bottle or can of beer is typically consumed by the beer within 24 hours of packaging, the noticeable presence of a stale flavor generally does not appear for several weeks.

In the past, the stale flavor of oxidized malt beverages, such as beer, generally has been attributed to the combined effects of oxidation, light and heat. Most investigators have focused on methods of reducing oxidation in the finished product. For example, the present practice of delaying the staling of beer includes maintaining a low level of air (or oxygen) in the packaged beer by minimizing free head space. Modern beer-filling machines are designed to achieve very low air levels in the packaged product. Typically, the bottle is evacuated before it is filled with beer, or the air in the evacuated bottle is replaced with carbon dioxide before filling, or overfoaming the bottle is utilized to displace the head space gases with beer foam. All of these practices can produce air levels of less than 0.5 ml. per 12 oz. bottle. But even these low levels of air still allow beer to oxidize in 2–3 months.

The off-flavors are made more obvious when the malt beverage has been stored at elevated temperature (thermal reactions). The negative influence of isohumulones and melanoidins on the oxidation of alcohols at elevated temperatures has been known for many years. See, e.g., Hashimoto, *Rept. Res. Lab. Kirin Brewery Co. Ltd.* 19:1 (1979). However, although beer is ideally stored at cold temperatures, maintaining a uniformly cool temperature is not always possible during transport. This is a particular problem in hot and humid countries where the temperature averages 28–38° C., even more so in those countries where modern refrigeration is not always available. Therefore, there is clearly a need for a reliable method of stabilizing beer flavor, which does not rely upon specifically controlled environmental conditions after the packaged product has left the brewery.

The Maillard Reaction

More than eighty years ago, Louis Maillard first investigated the reaction of reducing sugars with the free amino groups of amino acids and proteins. This complex reaction, termed the Maillard reaction, or non-enzymatic browning, is responsible for the aroma and taste in cooked or preserved foods. Specifically, it is know to be involved in the resulting color and aroma of fermented malt beverages, such as beer or sake.

As diagramed in FIG. 1, the Maillard reaction is initiated by the reaction of primary amines (from amino acids, proteins and nucleic acids) with sugars to form imines (Schiff bases) which undergo further rearrangement to form the Amadori products, which are responsible for the browning and fluorescent process, which subsequently results in the formation of numerous advanced glycosylation end products. Broadly, the advanced glycosylation end products are termed α-carbonyl intermediates, including, for example, 1-deoxydiketoses and 3-deoxyaldoketoses. When the reduced sugar is glucose, as in the brewing of malt, one of the a-carbonyl intermediates is 3-deoxyglucosone.

Hundreds of compounds, including dextrins, polypeptides, alcohols, polyphenols, pyrrols, isohumulones, melanoids, fatty acids and aldehydes, as well as related precursors and intermediates, are involved during the brewing process in the Maillard reaction. For example, there are over 140 reductases and dehydrogenases in the superfamily of reductases involved in the Maillard reaction.

A wide range of carbonyl compounds are known to be reduced via the Maillard reaction during fermentation, particularly from malt and wort, and to produce off-flavors (see Meilgaard et al., *Tech. Q. Master Brew. Assoc. Am.* 12:151–168 (1975)). Two biological pathways control the level of carbonyl compounds in the final product—the formation of aldehydes from the oxyacid pools and the enzymatic removal of wort carbonyls by the brewer's yeast.

Higher alcohols and the corresponding aldehydes are formed partly by anabolic processes from the main carbon source and partly through the catabolic pathway from exogenous amino acids. In addition, aldehydes produced during fermentation, mashing and boiling are known to be potential substrates for aldehyde dehydrogenases or reductases. Peppard et al, *J. Inst. Brew.* 87:386–390 (1981). However, recent studies have indicated that aldehyde-reducing systems are be more complex than previously assumed. See Collins et al., *Proc. Congr. Eur. Brew. Conv.* 23:409–416 (1991); Kronlof et al., *Proc. Cong. Eur. Brew. Conv.* 22:355–362 (1989). It is now recognized that many enzymatic systems are involved in the reduction of the carbonyl compounds into higher alcohols, and that each system probably operates with varying activities during the course of the fermentation process (Debourg et al., *J. Am. Soc. Brew. Chem.* 52(3):100–106 (1994). For example, carbonyl compounds, particularly unsaturated carbonyls, are not stable. Such compounds are decomposed to shorter chains, which are subject to aldol condensation.

Unsaturated aldehydes, notably trans-2-nonenal, and related compounds involved in the oxidation of long-chain fatty acids have long been associated with stale flavor in beer. See, e.g., Debourg et al., supra, and U.S. Pat. No. 4,110,480. It is well known that enzyme mediated oxidation of unsaturated fatty acids, such as linoleic acid, followed by the subsequent oxidative or non-oxidative scission of the carbon chain, will produce flavor-active compounds having carbon lengths of 6 to 12. Therefore, those attempting to stabilize fermented malt beverage flavor have, in some cases, focused on modifying the lipids involved in the brewing process. However, in beer, the lipids are derived from malt in various forms including simple lipids (fatty acids, triglycerides and other neutral lipids), complex lipids (glycolipids and phospholipids) and bound lipids such as those bound with starch grains.

Numerous methods have been attempted to remove lipids from the raw materials, including (1) removal of the germ of the grain, which contains a significant portion of lipids found in the raw material cereals (polishing), (2) removal of lipids from the raw material cereals by ethanol extraction, (3) pretreatment of the raw material cereal grains with a lipid decomposing enzyme (Japanese Patent Examined Publ. No. 22478/1973, Japanese Patent Unexamined Publ. No. 55069/1987), and (4) removal of lipids by special filtration-separation (U.S. Pat. No. 5,460,836). However, not all lipids have an adverse effect, i.e., the balance of these forms of lipids subtly affects the beer quality and the efficiency of beer brewing process. Thus, even after years of study, it remains unknown what balance is appropriate, or how altering the total lipid content will affect the stability of flavor in the stored, finished product.

Another recognized technique for stabilizing beer against oxidation is to add an oxygen scavenger, such as sulfur dioxide, usually in the form of bisulfite, to the beer. Sulfur dioxide is produced by yeast during fermentation and will combine with carbonyls to form bisulfite addition components that are hydrophilic, and thus less volatile. However, although effective, increasing the concentration of $SO_2$, naturally or artificially, may be commercially unacceptable. In the United States, for example, $SO_2$ is limited by law to less than 10 ppm, and even those low levels produce undesirable and sulfury aromas in some beers. In other countries, such as Germany, any addition of exogenous $SO_2$ is strictly prohibited.

Even if permitted, the addition of bisulfite, which works by binding to aldehydes, is not an ideal solution. Beer is a complex product, comprising many different aldehydes (notably acetaldehyde, a normal by-product of fermentation), hence the action of a sulfite additive is often muted. The addition of other oxygen scavengers has also been tried, but with little effect on the long-term stability of the flavor in the fermented malt beverage.

In spite of all of the available art and years of research, however, beer flavor still goes stale. Thus, it is clear that until the present invention, there remained a long-felt need in the art for a reliable method of stabilizing the flavor of fermented malt beverages, which has the following characteristics: (1) will not significantly alter the desirable fresh flavor of the finished product, (2) will not significantly diminish the efficiency of the brewing process, (3) violates no law or regulation regarding the addition of additives or preservatives, and (4) is not dependent on maintaining specific environmental conditions for the transportation and storage of the packaged product.

SUMMARY OF THE INVENTION

The present inventors, deducing that the products formed during the Maillard reaction could be used as indices of beer aging, developed a method (using indices measured by a combination of capillary electrophoresis and HPLC techniques) to reliably monitor flavor stability and the organoleptic effect of aging on beer (Bravo et al., *IBTC Technical Consortium Meeting* #35, Salzburg, Austria, September 1993; Bravo et al., *IBTC Technical Consortium Meeting* #36, Caracas, Venezuela, November 1994). By utilizing the method for the detection of the relevant chemical indices, a novel system was developed, significantly advanced over those described and used heretofore, for dependably and efficiently assessing the degree of beer freshness, and for determining the storage conditions (time and temperature) of a beer exposed to a previously unknown environment. Furthermore, these analytical systems have been utilized to develop methods for improving the flavor stability of malt beverages such as beer, and for producing malt beverages by these methods.

In initial investigations designed to solve the above-described problems, it was discovered that by enzymatically regulating the production of certain intermediates of the Maillard reaction formed during the brewing process, a fermented malt beverage could be reliably produced having a refreshingly clean taste and enhanced flavor stability. The present inventors made further investigations based on this finding, and developed the present invention.

The present inventors have developed an entirely new method for stabilizing fermented malt flavor by focusing on an aspect of the brewing reaction not previously considered in the prior art. The present invention is therefore directed to the stabilization of the flavor of a fermented malt beverage using one or more inhibitors, blockers, reducing agents or binding agents that inactivate Maillard reaction intermediates; such agents may include, for example, NADPH-dependent oxidoreductase enzymes or chemical agents such as aminoguanidine.

In order to evaluate flavor stability, the inventors found it essential to have a sensitive, quick and reproducible method by which changes in the flavor of the beer could be analyzed. Sensory testing has been the traditional means available for assessing the organoleptic quality of beer. Taste testing, although sensitive, suffers from human limitations, such as personal bias and the tendency to make comparative (subjective) rather than objective evaluations (Mathews et al., *Trends in Food Science & Technol.* 4:89–91 (1990)). The Institute of Brewing Technology began using high performance liquid chromatography (HPLC) analyses according to e.g., Greenhoff and Wheeler, *J. Inst. Brew* 86:35 (1981); Strating and Drost, *Dev. in Food Sci.* 17:109–121 (1988). Improved methods utilizing purge and trap techniques, gas chromatography, and mass selective detection using the SIM technique were applied to establish higher capacity and better separation, determination and identification. See, e.g., Narziβet al., *MBAA Tech. Q.* 30:48–53 (1993). However, objective measurements of a particular quality parameter are meaningless unless they are correlated to the human response to the beverage as a whole when it is purchased and consumed under normal conditions.

Thus, the present inventors developed a system by which the organoleptic deterioration of beer could be evaluated by analytical indices providing a series of compounds (see FIG. 2) representing a reproducible continuum of fresh through deteriorated (stale) forms. These analytical indices were then related to organoleptic evaluations, as demonstrated in FIGS. 3A and 3B, to provide a correlation between objective and organoleptic measures of flavor freshness. Bravo et al., *IBTC Technical Consortium Meeting* #35, Salzburg, Austria, September 1993; Bravo et al., *IBTC Technical Consortium Meeting* #36, Caracas, Venezuela, November 1994. These compounds participate in the reactions involved in the beer staling process (substrates, intermediates or final products), but do not necessarily produce the stale flavor. These analytical indices are relatively easy to detect and show a significant change in their relative peak areas during the aging process (see FIGS. 3A and 3B).

The concentration of furfural, 5-methylfurfuryl, 2-acetylfuran and 5-hydroxymethylfurfural (5-HMF) are useful indices for measuring heat damage in beer. For example, in an effort to establish a "quality deterioration test," methods have been developed for detecting furfural and 5-methylfurfuryl in fruit juices during storage. Harayama et al., *Agric. Biol. Chem.* 55:393–398 (1991) found by multivariate analysis of off-flavor in head-space volatiles formed during the storage of beer, that certain furfural compounds were a valuable index for measuring a particular cardboard flavor in the beer. Grongvist et al., *EBC Cong.* 421–428 (1993), using gas chromatography to measure carbonyl compounds present during beer production and aging, found that the concentration of furfural was significantly increased during aging.

The present invention is directed to the production of malt beverages having improved flavor stability. The invention has particular utility in the production of fermented malt beverages such as beer, although the invention also may be advantageously used in the production of other malt flavored beverages. The invention is further directed to brewing methods for producing fermented malt beverages, such as beer, the beverages prepared by said method, and beverages having a substantially stabilized flavor.

In particular, the present invention is directed to a method for stabilizing the flavor of a fermented malt beverage, most particularly a beer, by the addition of one or more reductase enzymes including, but not limited to, oxidoreductases such as aldehyde reductases (EC 1.1, including aldose reductases, aldocarbonyl reductases and oxoaldehyde reductases), keto reductases (EC 1.2, including ketose reductases and keto-carbonyl reductases), acetyl reductases (EC 1.3), primary aminoreductases (EC 1.4), secondary aminoreductases (EC 1.5) and particularly NADH/NADPH oxidoreductases (EC 1.6, most particularly isozymes of Old Yellow Enzyme (OYE; EC 1.6.99.1) such as OYE1 (SEQ ID NO:1), OYE2 (SEQ ID NO:2) and OYE3 (SEQ ID NO:3)). The invention also relates to fermented malt beverages (particularly beers) prepared by these methods, and to fermented malt beverages (particularly beers) having enhanced flavor stability.

The invention further relates to the use during the brewing process of reductase enzymes such as those described above from naturally occurring sources (e.g., yeast cells such as Saccharomyces spp. cells and particularly *Saccharomyces cerevisiae* and *Saccharomyces carlsbergensis* cells), to stabilize the flavor of the resulting fermented malt beverage and to produce a fermented malt beverage having a stable flavor. It also relates to microorganisms, particularly yeasts, bacterial cells and animal cells (including insect cells) which have been specifically modified, selected, or genetically engineered to express or secrete one or more of the above-described reductase enzymes which may be used during the brewing process to stabilize the flavor of the resulting fermented malt beverage and to produce a fermented malt beverage having a stable flavor.

The present invention also provides enzymatic digests from naturally occurring sources (e.g., yeast cells) or from genetically modified cells (e.g., the genetically modified yeast, bacterial or animal cells described above), or extracts thereof, which will provide a sufficient amount of the necessary enzymes to block, inhibit or reduce the Maillard reaction intermediates (e.g., 3-deoxyglucosone), which results in the formation of the stale flavor in fermented malt beverages.

The present invention also provides methods for enhancing the flavor stability of a malt beverage. In accordance with the present invention, these methods are suitable for enhancing the flavor stability of a fermented malt-beverage, in particular a beer. Thus, it is an object of the present invention to provide methods of brewing or preparing beer, wherein the flavor stability of the beer is enhanced. A first such method of the invention comprises adding one or more of the above-described natural sources (e.g., yeast cells), genetically modified sources (e.g., genetically modified yeast, bacterial or animal cells), enzymatic digests or extracts, or purified reductase enzymes, and one or more reductase enzyme cofactors (such as NADH or NADPH) to the grain malt, wort mixture (prior to or following fermentation) or fermented malt beverage (prior to or following processing), under conditions that favor the enhancement of flavor stability in the finished fermented malt beverage. A second such method of the invention comprises immobilizing the above-described enzyme sources, digests or extracts, or purified enzymes, and reductase enzyme cofactors, on a solid support and contacting the grain malt, wort mixture (prior to or following fermentation) or fermented malt beverage (prior to or following processing) with these immobilized reductase enzymes/cofactors under conditions that favor the enhancement of flavor stability in the finished fermented malt beverage. According to this aspect of the invention, the solid support may be a membrane (such as nitrocellulose, diazocellulose, nylon, etc.), a bead (such as an alginate bead, a polystyrene bead, a latex bead, a glass bead, a magnetic or paramagnetic bead, etc.), a polystyrene plate, and the like. Most preferred are membranes and beads. In a particularly preferred embodiment of this aspect of the invention, one or more enzyme cofactors such as NADH or NADPH, and one or more isozymes of the NADPH oxidoreductase OYE (EC 1.6.99.1) such as OYE1 (SEQ ID NO:1), OYE2 (SEQ ID NO:2) or OYE3 (SEQ ID NO:3) or cells (natural or genetically modified) or extracts there of comprising one or more OYE isozymes, are immobilized onto a solid support and used in the methods of the invention to produce a fermented malt beverage, particularly a beer, having enhanced flavor stability.

The invention further provides the malt beverages produced by these methods. In accordance with the present invention, the malt beverage may a fermented malt beverage, particularly a beer. Thus, it is an object of the present invention to provide a beer in which the flavor stability has been enhanced.

Other preferred embodiments of the present invention will be apparent to one of ordinary skill in light of the following drawings and description of the invention, and of the claims.

A: Graph demonstrating changes in the intensity of LC18 peak height during the storage at 5° C. and its correlation with flavor evaluation. LC18 is consumed at low temperatures and tends to disappear in time.

B: Graph demonstrating changes in the concentration of 5-HMF during the storage of beer at 28° C., and its inverse correlation with the oxidation degree.

Figure 4:
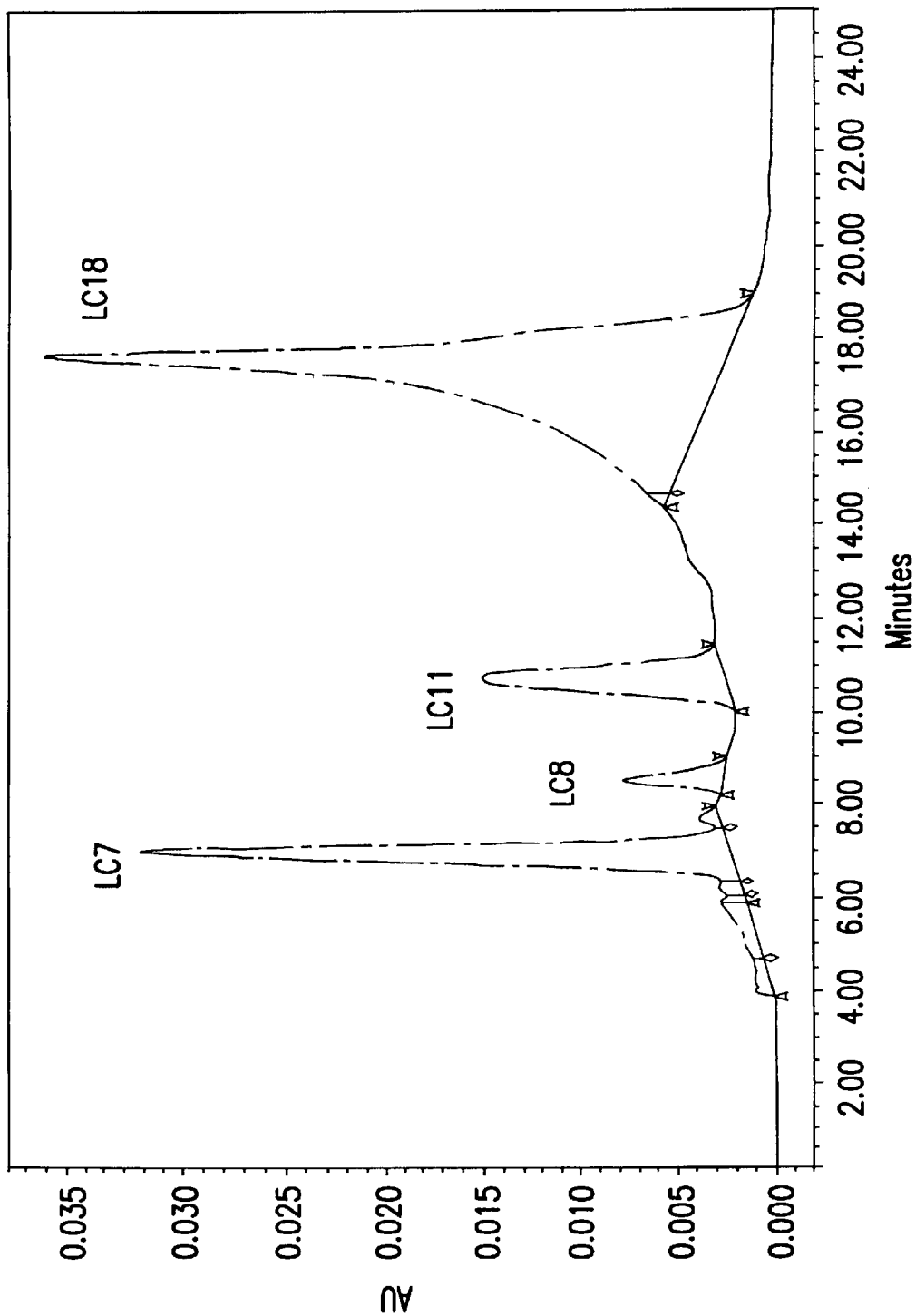

FIG. 4. Chromatogram of a heat-treated glucose-glycine model system, consisting of 1 M glucose +0.5 M glycine, after 3 hours of reaction at 90° C., demonstrating acquisition of the analytical indices of beer aging (LC8, LC11 and LC18) in a model system.

Figure 5:
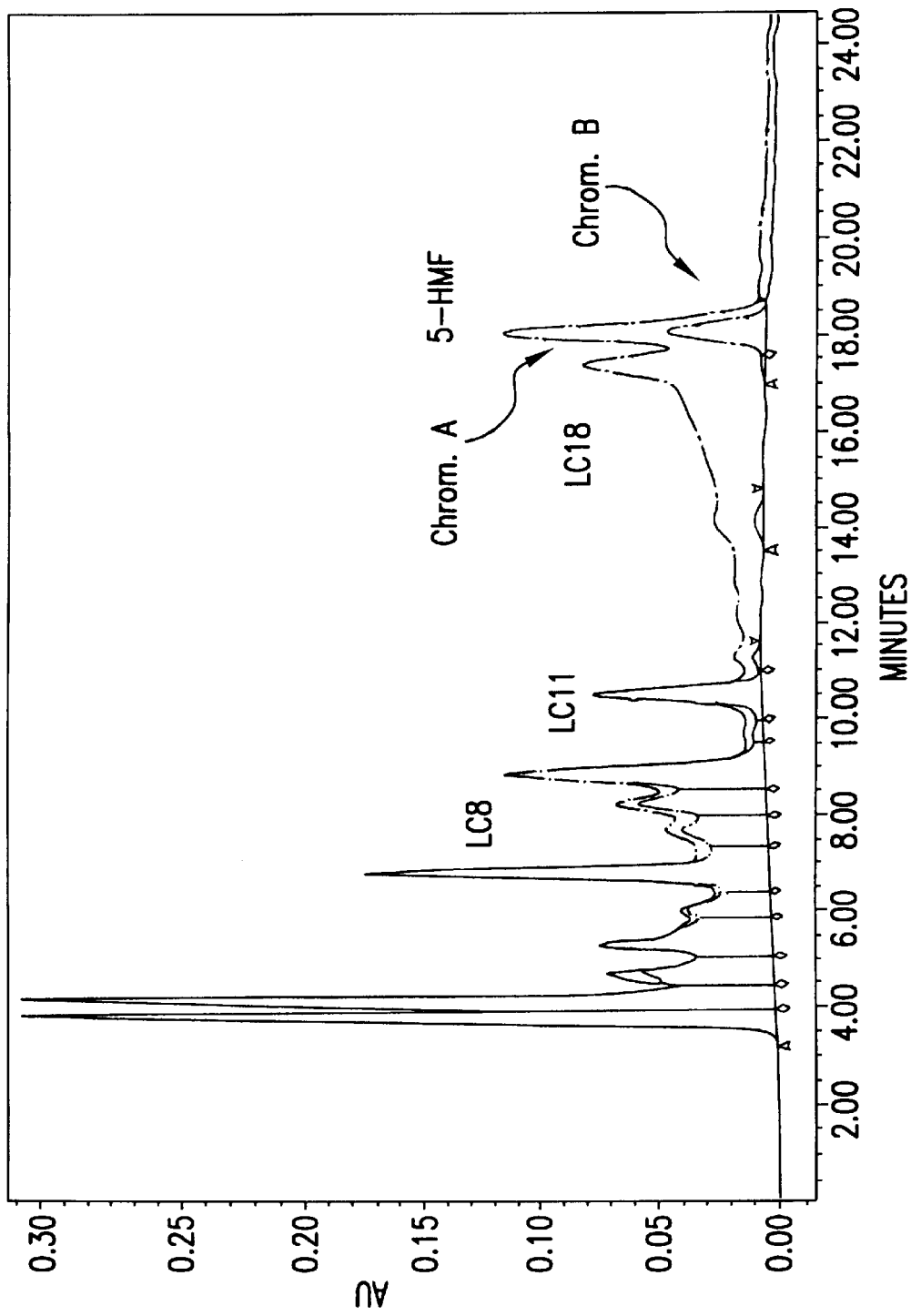

FIG. 5. Composite chromatogram demonstrating the effect of the addition of 1,2-phenylenediamine to wort. A: wort. B: wort+1,2-phenylenediamine. The addition of 1,2-phenylenediamine causes a specific reduction in the LC18 peak.

FIG. 6.

a: Bar graph demonstrating changes in the area of hydrophobic quinoxalines accompanying storage of beer at 5° C. and 28° C. for 15 days and at 60° C. for 3 days.

b: Bar graph demonstrating changes in the area of hydrophilic quinoxalines accompanying storage of beer at 5° C. and 28° C. for 15 days and at 60° C. for 3 days.

Figure 7:
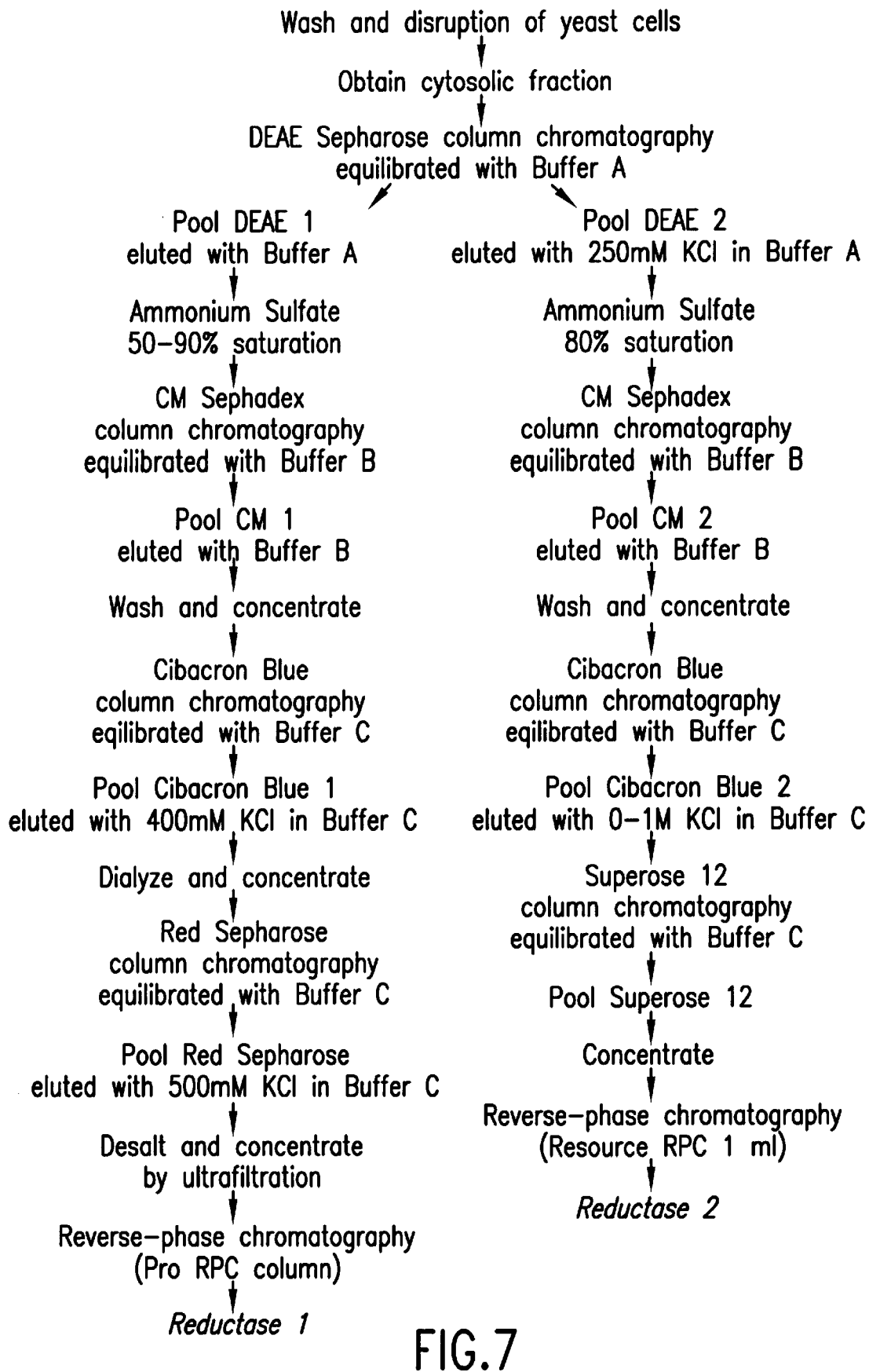

FIG. 7. Scheme of reductase enzyme purification procedure. Buffer A: 25 mM potassium phosphate pH 7.5. Buffer B: 5 mM potassium phosphate pH 6.5. Buffer C: 25 mM potassium phosphate pH 7.0.

Figure 8:
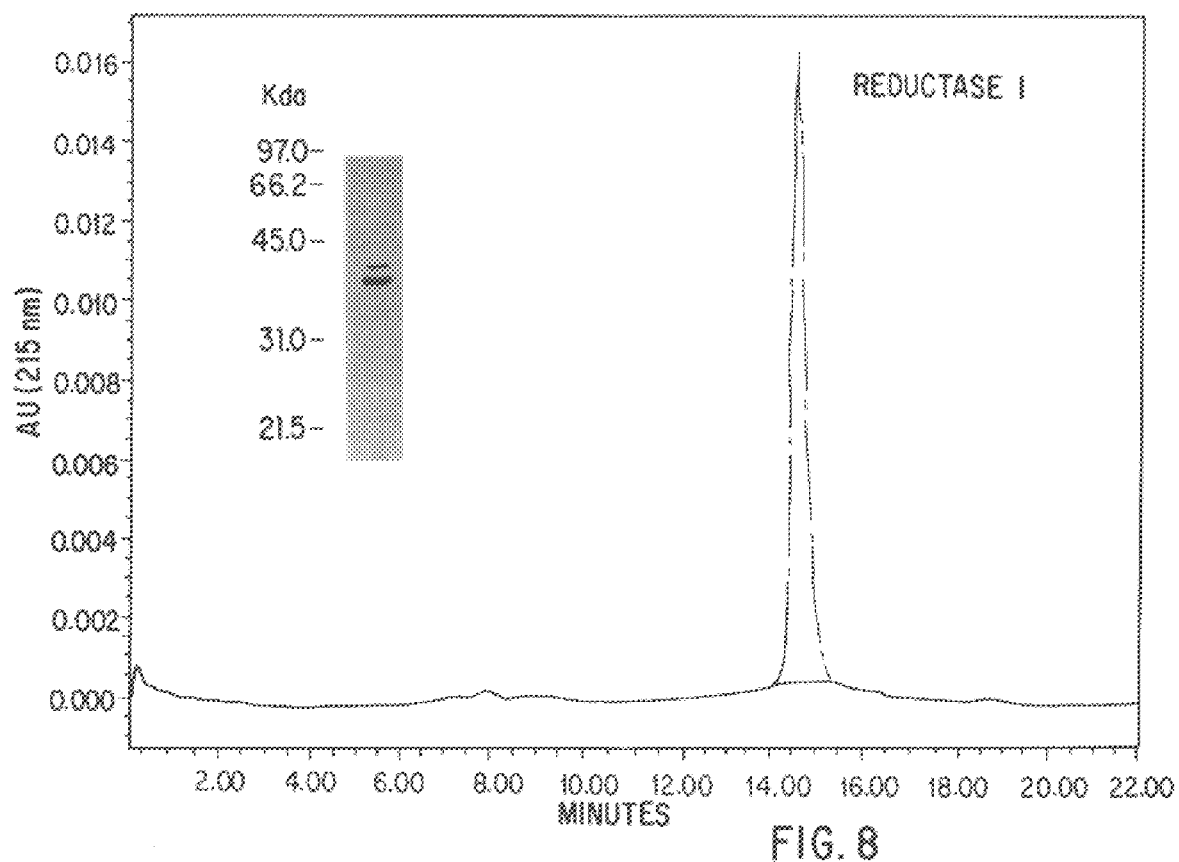

FIG. 8. Elution profile of Reductase 1 on Sephacryl S-200 chromatography. Inset: SDS-polyacrylamide gel electrophoresis of Reductase 1. The gel was stained with Coomassie Brilliant Blue.

Figure 9:
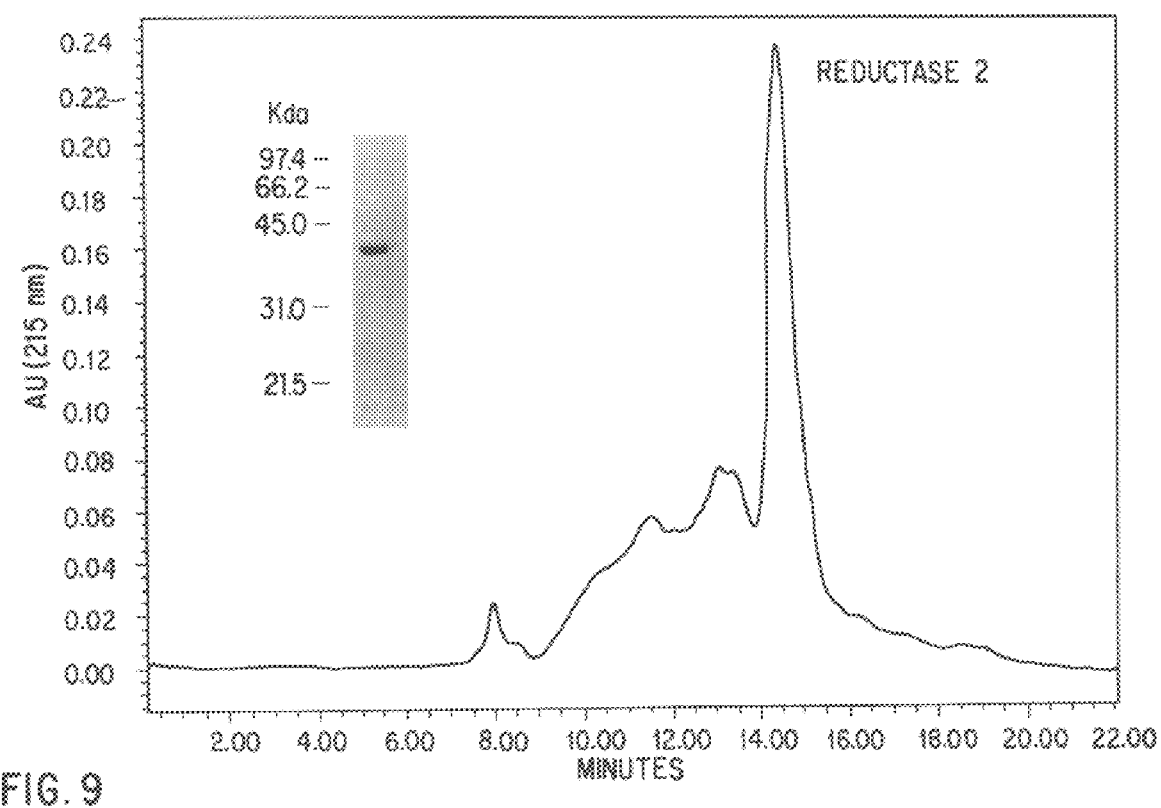

FIG. 9. Elution profile of Reductase 2 on Sephacryl S-200 chromatography. Inset: SDS-polyacrylamide gel electrophoresis of Reductase 2. The gel was stained with Coomassie Brilliant Blue.

FIG. 10. Substrate specificities of the Reductase 1 and Reductase 2 enzymes.

Figure 11:
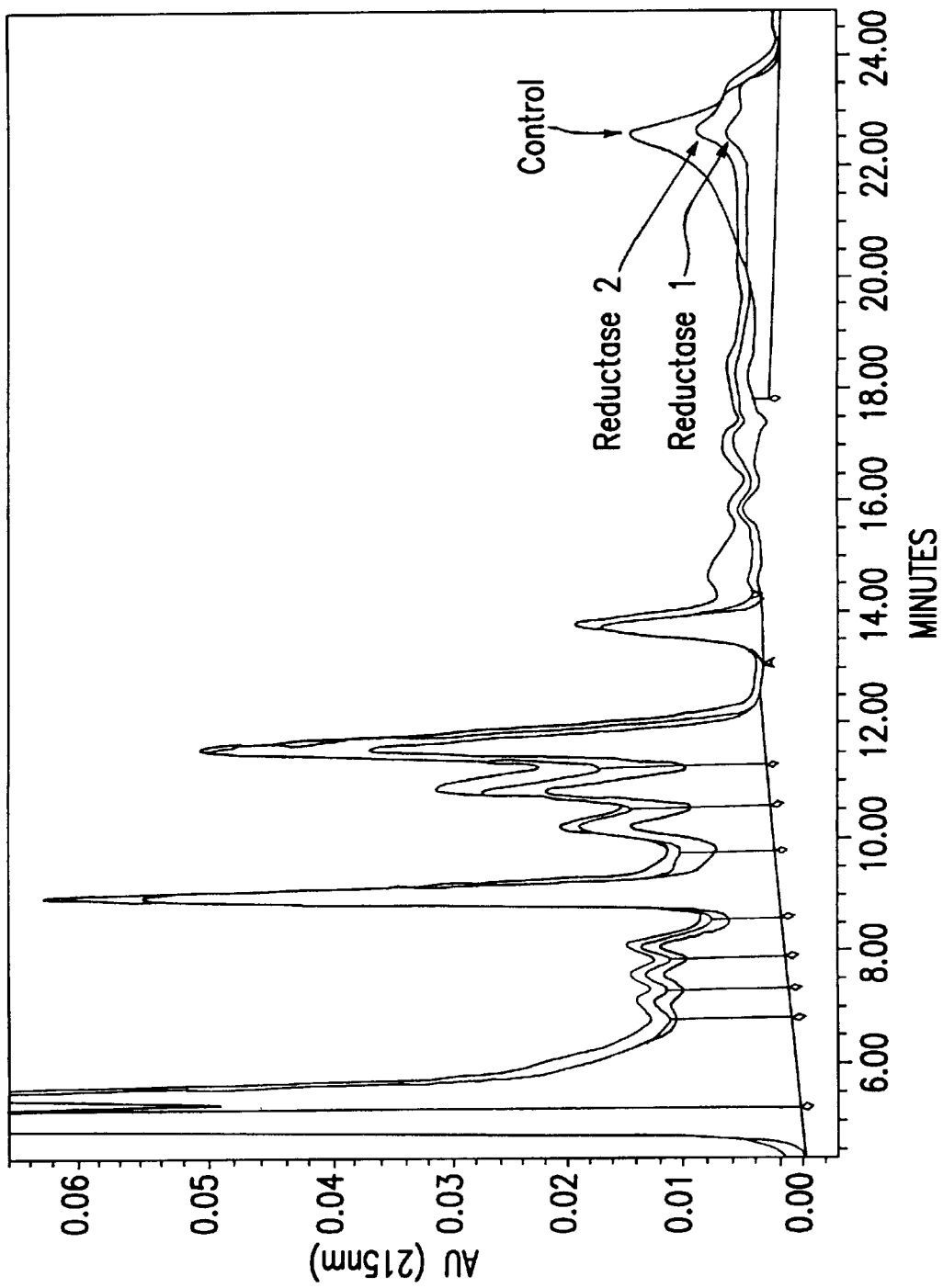

FIG. 11. Composite chromatogram demonstrating the decrease in the LC18 peak in beer after addition of Reductases 1 and 2 isolated from brewer's yeast.

Figure 12B:
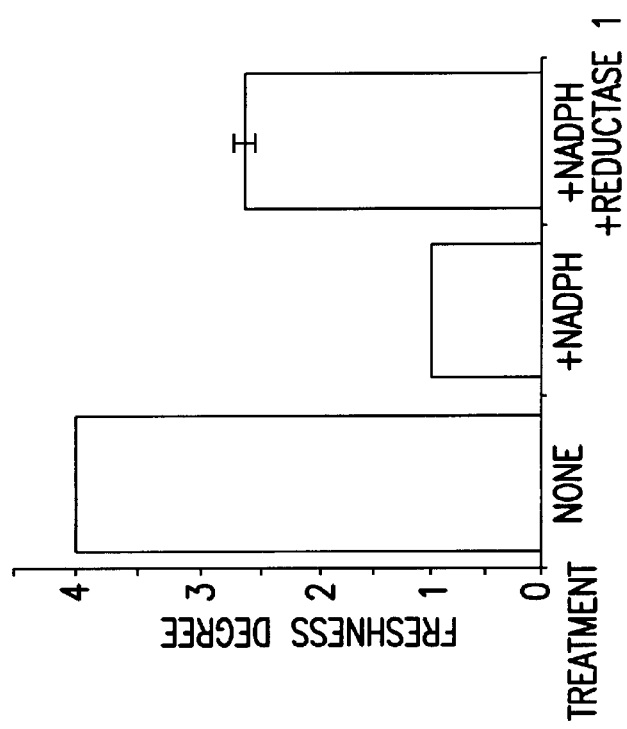
Figure 12A:
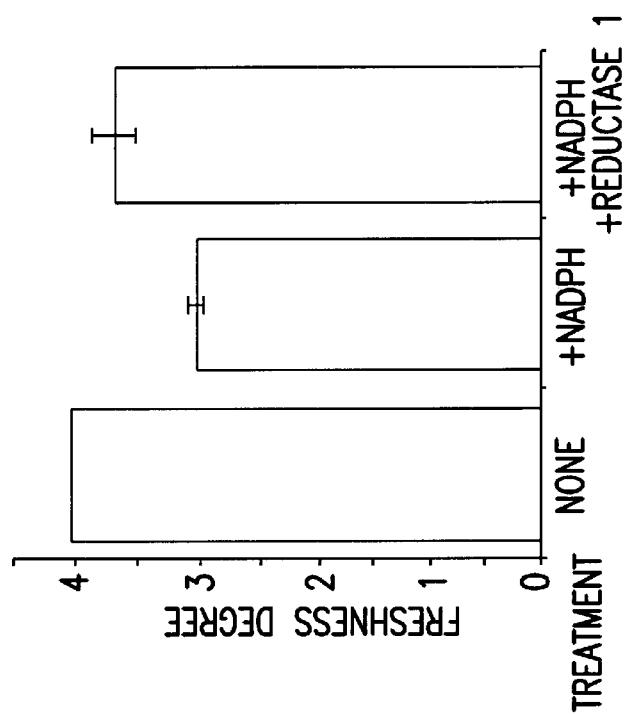

FIG. 12. Bar graphs demonstrating organoleptically determined freshness degree of beers treated with Reductase 1. Beers were incubated with a mixture of buffer C, NADPH (control beers) and Reductase 1 (experimental beers) for 15 days at 28° C. (panel a) or 3 days at 60° C. (panel b).

DETAILED DESCRIPTION OF THE INVENTION

Definitions

Throughout this disclosure, various terms that are generally understood by those of ordinary skill in the applicable arts are used. Several terms are used with specific meaning, however, and are meant as defined by the following:

As used herein, the term "malt" is meant to refer to any cereal grain, particularly barley, steeped in water until it is sprouted and used in brewing and distilling.

The term "mash" as used herein is defined as crushed malt or grain steeped in hot water to make wort.

The term "wort" as used herein is defined as the liquor run-off after extracting a prepared solid material, such as a cereal grain or malt, with hot water.

As used herein, the term "fermented malt beverage" is meant as any malt-flavored beverage produced by fermentation, such as beer or sake.

As used herein, the term "beer" is defined as an alcoholic beverage brewed from malt and hops. The term as used herein is meant to include ales, stouts, lagers, porters, malt liquors, low-calorie, low-alcohol and light brews, and the like.

Figure 1:
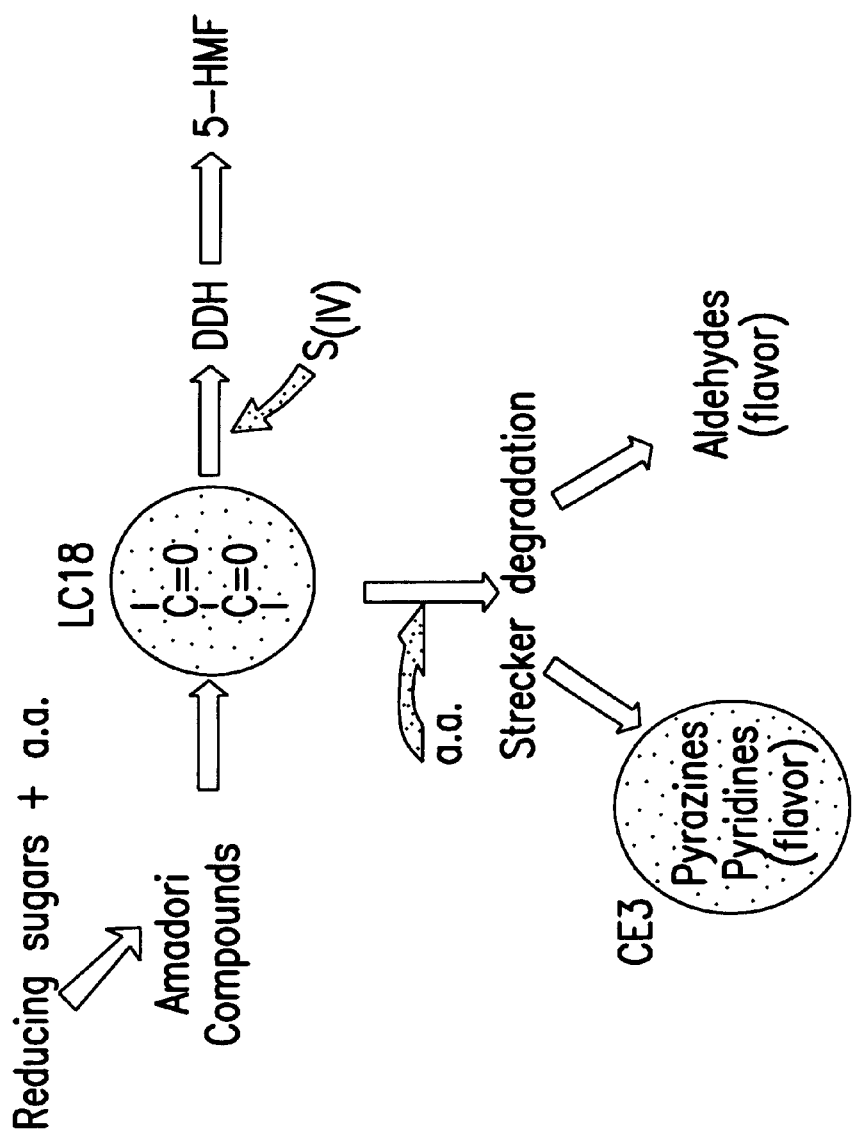
FIG. 1. Diagram of the Maillard Reaction, the proposed mechanism of formation of LC 18 in beer, and its possible involvement in flavor deterioration. LC18 is a dicarbonyl compound precursor of 5-HMF which can also condense with amino acids through the Strecker degradation to produce aldehydes and pyrroles or pyrazines (CE3).
Figure 2:
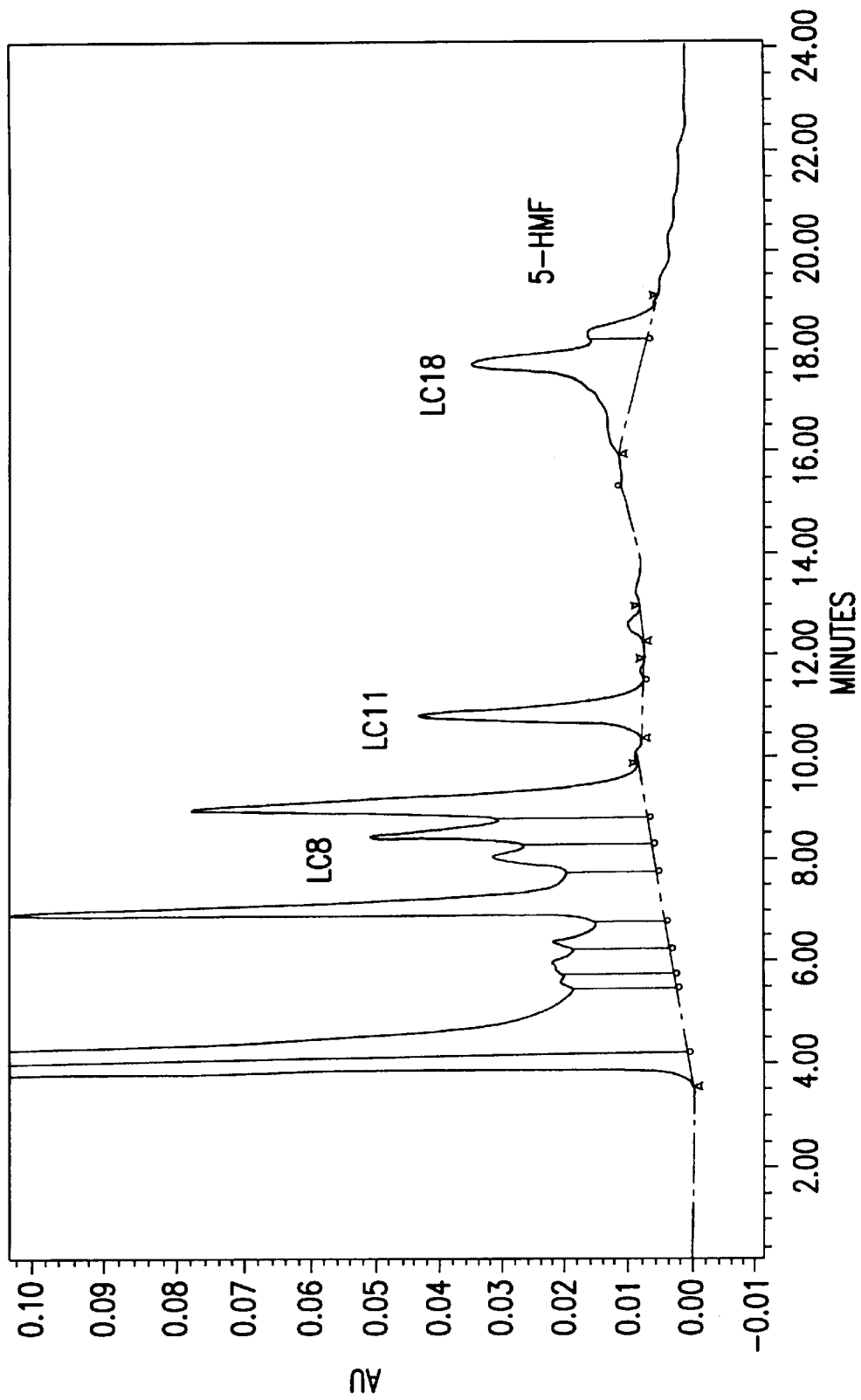
FIG. 2. Chromatogram of fresh beer showing the chemical indices of beer aging: LC8, LC11, LC18 and 5-HMF.
Figure 3B:
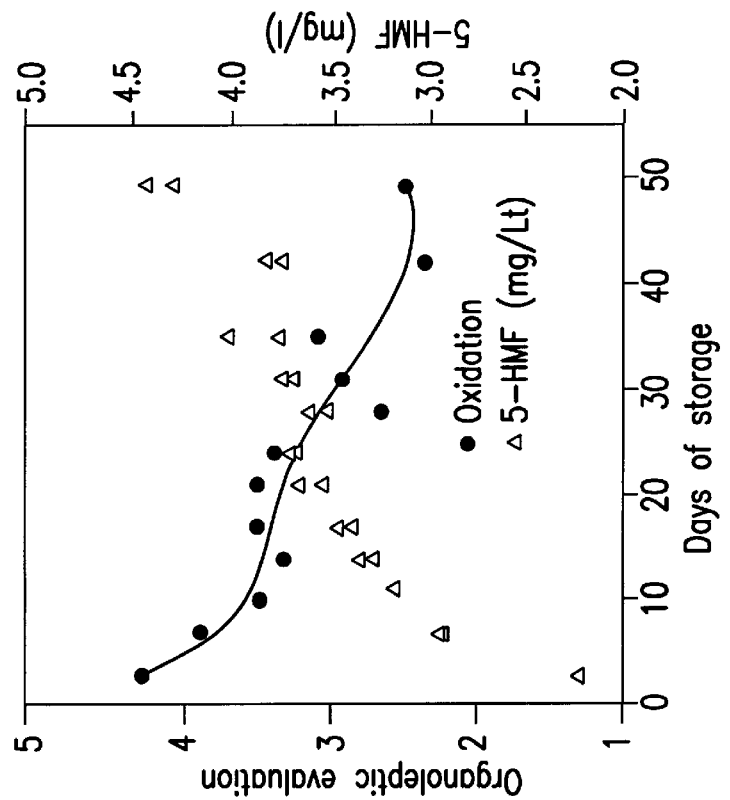
FIG. 3.
Figure 3A:
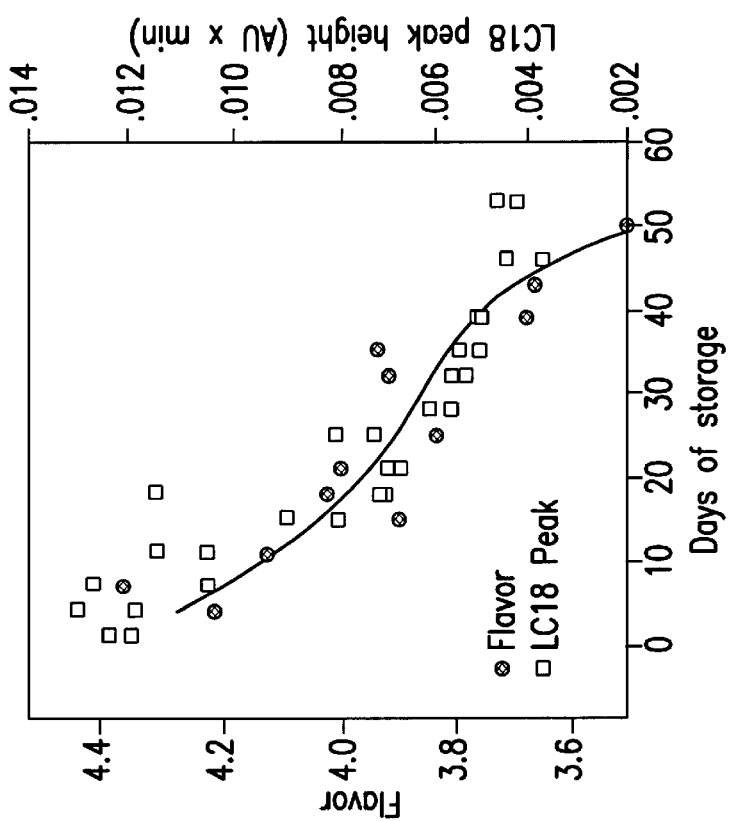

Prior to the present invention there was no suggestion in the art that, by enzymatically regulating the production of one or more specific intermediates of the Maillard reaction (see FIG. 1), the flavor of beer could be effectively stabilized. In addition, the use of a specific reductase as a regulatory enzymatic processing aid in the production of beer has not heretofore been suggested. Historically, most assays used to test the flavor stability of beer have been purely subjective (e.g., classical panels of beer tasters) and have not been conducive to quantitation. It was therefore necessary for the present inventors to first develop a reliable, objective analytical assay to determine flavor stability of a sample, which could be used in addition to organoleptic evaluations, before new procedures could be implemented or additives characterized in terms of their effects on flavor stability.

The invention therefore relates to methods for stabilizing the flavor of a fermented malt beverage, such as a beer, and to fermented malt beverages such as beers produced by such methods. The methods of the invention typically comprise the use of one or more inhibitors, blockers, reducing agents or binding agents to inhibit, block, reduce, bind or otherwise inactivate one or more Maillard reaction intermediates that are involved in causing staling of the flavor of fermented malt beverages. The inhibitors, blockers, reducing agents and binding agents used in the present methods may be any agent, compound, composition, etc., that effectively inhibits, blocks, reduces, binds or otherwise inactivates one or more Maillard reaction intermediates thereby stabilizing the flavor of a fermented malt beverage. Such agents may include, but are not limited to, enzymes (particularly reductase enzymes), enzyme complexes, cells (particularly yeast cells such as those of the Saccharomyces genus), enzyme-containing extracts or digests of cells, enzyme-cofactor complexes or chemical agents such as aminoguanidine. Particularly preferred are enzymes and chemical agents.

Thus, one preferred aspect of the present invention provides a method wherein a flavor-stabilizing amount of at least one reductase enzyme is used as an additive to the fermented malt beverage. This enzyme additive provides enhanced stabilization of the flavor of the finished fermented malt beverage. Reductase enzymes suitable for use in these methods of the invention include, but are not limited to, oxidoreductases such as aldehyde reductases (EC 1.1, including aldose reductases, aldocarbonyl reductases and oxoaldehyde reductases), keto reductases (EC 1.2, including ketose reductases and ketocarbonyl reductases), acetyl reductases (EC 1.3), primary aminoreductases (EC 1.4), secondary aminoreductases (EC 1.5) and particularly NADH/NADPH oxidoreductases (EC 1.6, most particularly isozymes of Old Yellow Enzyme (OYE; EC 1.6.99.1) such as OYE1 (Saito, K., et al., *J. Biol. Chem.* 266(31):20720–20724 (1991); SEQ ID NO:1), OYE2 (Stott, K., et al., *J. Biol. Chem.* 268(9):6097–6106 (1993); SEQ ID NO:2) and OYE3 (Niino, Y. S., et al., *J. Biol. Chem.* 270(5):1983–1991 (1995); SEQ ID NO:3). It is to be understood, however, that any reductase enzyme that is effective at stabilizing the flavor of a fermented malt beverage may be used in the present methods to produce the present fermented malt beverages.

In one embodiment of the invention, the reductase enzyme(s) may be added at any stage of the brewing process, including to the grain malt, to the wort prior to fermentation, to the fermented wort, to the fermented malt beverage prior to processing, or to the processed fermented malt beverage prior to packaging. Most preferably, the reductase enzyme is added to the wort prior to fermentation, to the fermented malt beverage prior to processing, or to the processed fermented malt beverage prior to packaging.

Preferably, the reductase enzymes are naturally occurring. The enzymes may be isolated using known protein extraction procedures from a number of sources, and may be purified as described below and then added to the fermentation beverage as a processing aid and/or as an additive. In this scheme, the reductase enzymes may be added to the fermentation process continuously or as a single injection. The methods of the present invention may be carried out using either full-length enzymes, or biologically active fragments thereof. As an alternative form of the enzyme, certain synthetically formulated, full-length or attenuated reductase enzymes can be used in place of the naturally occurring enzymes to stabilize the flavor of the fermented malt product, so long as the alternative enzyme form possesses the biological activity of the naturally occurring reductase enzyme.

In one particularly preferred aspect, the reductase enzyme isolated, purified and/or used in the methods of the present invention is an oxidoreductase enzyme, including but not limited to an aldehyde reductase (EC 1.1, including aldose reductases, aldocarbonyl reductases and oxoaldehyde reductases), a keto reductase (EC 1.2, including ketose reductases and ketocarbonyl reductases), an acetyl reductase (EC 1.3), a primary aminoreductase (EC 1.4), a secondary aminoreductase (EC 1.5) or an NADH/NADPH-dependent oxidoreductase (EC 1.6, most particularly isozymes of Old Yellow Enzyme (OYE; EC 1.6.99.1) such as OYE1 (SEQ ID NO:1), OYE2 (SEQ ID NO:2) and OYE3 (SEQ ID NO:3)). Most preferably, the reductase enzyme is an isozyme of OYE (EC 1.6.99.1) such as OYE1 (SEQ ID NO:1), OYE2 (SEQ ID NO:2) or OYE3 (SEQ ID NO:3).

Naturally occurring reductase enzymes are preferably isolated from yeast cells using routine protein extraction procedures as set forth in Example 1 below, or from animal or vegetable sources. Preferred as sources of naturally occurring oxoaldehyde reductase enzymes are yeast cells, including brewer's or pitching yeasts, e.g., of the genus Saccharomyces, most preferably of the species *Saccharomyces cerevesiae* or *Saccharomyces carlsbergensis*.

The reductase enzymes isolated from these natural sources may be purified by protein purification techniques that are routine to those of ordinary skill in the art. Preferably, the enzymes are purified by a combination of "salting out" and chromatographic purification such as liquid chromatography, HPLC, FPLC, affinity chromatography, ion exchange chromatography, size exclusion chromatography, and immunoaffinity chromatography. Most preferably, the purified enzymes are purified by a combination of ammonium sulfate precipitation and HPLC or FPLC purification. These purified reductase enzymes may then be added to the product, in flavor-stabilizing amounts as described above, to enhance the flavor stability of the fermented malt beverage.

In an alternative embodiment, crude preparations of one or more of the above-described reductase enzymes may be added to the product without purification. Crude preparations encompassed by this embodiment of the invention include extracts or digests of naturally occurring yeast, animal or plant sources. Preferable is an extract or enzymatic digest of naturally occurring or genetically modified (as described below) cells. Methods for preparing such extracts or enzymatic digests are well-described in the microbiological literature (see, e.g., Difco Manual, Difco, Inc., Norwood, Mass.).

In another alternative embodiment, sources (such as yeasts) capable of producing one or more of the above-described reductase enzymes may be added per se in an amount sufficient to produce an effective amount of the oxoaldehyde reductase in situ to stabilize the flavor of the finished product. These sources may also be used to prepare a crude preparation, preferably an extract or enzymatic digest, comprising enhanced amounts of one or more of the above-described reductase enzymes, which is then used as described above to stabilize the flavor of a fermented malt beverage. Preferably, yeasts of the genus Saccharomyces, and most preferably of the species *Saccharomyces cerevisiae* or *Saccharomyces carlsbergensis*, are used in this embodiment.

In yet another embodiment, a variety of cells may be genetically modified to produce enhanced amounts of one or more of the above-described reductase enzymes relative to their parental or wild-type strains. Preferred cells for use in this aspect of the invention include, but are not limited to: yeast cells such as those of the genus Saccharomyces (particularly *S. cerevisiae* or *S. carlsbergensis*); bacterial cells such as those of the genera Escherichia (particularly *E. coli*), Bacillus (particularly *B. cereus, B. sublilis* or *B. megaterium*) or Xanthomonas; and animal cells (particularly insect cells such as *Spodoptera frugiperda* Sf9 or Sf21 cells, or Trichoplusa spp. cells). Particularly preferred are Saccharomyces spp. cells that have been genetically modified to produce high levels of at least one reductase enzyme, preferably at least one oxidoreductase enzyme such as at least one NADPH-dependent oxidoreductase enzyme, and most preferably at least one enzyme selected from the group consisting of OYE1 (SEQ ID NO:1), OYE2 (SEQ ID NO:2) and OYE3 (SEQ ID NO:3). Methods for genetically modifying these cells and other microorganisms are well-known and routine to those of ordinary skill in the art (see, e.g., Sambrook, J., et al., *Molecular Cloning: A Laboratory Manual*, 2nd Ed., Cold Spring Harbor, N.Y.: Cold Spring Harbor Laboratory Press (1987); Watson, J. D., et al., in: *Recombinant DNA*, 2nd Ed., New York: Scientific American Books, pp. 235–253 (1992)). These genetically modified cells provide a readily available source of the above-described reductase enzymes (as a crude or purified preparation) which may be added as described above to stabilize the flavor of the fermented malt beverage. Alternatively, as in the previous embodiments, the genetically modified cells having enhanced reductase expression may be added per se in an amount sufficient to provide in situ stabilization of the flavor in the finished malt beverage.

If added per se, cells capable of producing one or more reductase enzymes may be immobilized onto a solid support, at a density sufficient to provide enough enzymatic activity to substantially stabilize the flavor of the finished fermented malt beverage. Thus, in another preferred aspect of the invention, one or more of the above-described inhibitors, blockers, reducing agents or binding agents, such as one or more of the cells producing reductase enzymes, one or more of the extracts or enzymatic digests, or one or more of the purified reductase enzymes, may be immobilized on a solid support to form an "active solid support." These active solid supports may then be used in the present methods of stabilize the flavor of a fermented malt beverage. In the case of enzymes, extracts, digests or cells, these compounds may be immobilized on the solid support in conjunction with one or more enzyme cofactors, such as NADH or NADPH, to produce an enzyme-containing solid support. By the term "solid support" is intended any solid support to which a cell, extract or enzymatic digest, or purified enzyme can be immobilized. By the term "active solid support" is meant a solid support upon which at least one inhibitor, blocker, reducing agent or binding agent that inactivates one or more Maillard reaction intermediates is immobilized. By the term "enzyme-containing solid support" is intended a solid support upon which at least one enzyme source (i.e., a cell producing an enzyme, a digest or extract comprising the enzyme, or a purified enzyme), and preferably the corresponding enzyme cofactor(s), have been immobilized. Solid supports that may be used in this aspect of the invention include, but are not limited to, membranes (such as nitrocellulose diazocellulose or nylon membranes), glass, polystyrene, polyvinylchloride, polypropylene, polyethylene, dextran, Sepharose, agar, starch, nylon, beads (particularly alginate, latex, glass, magnetic, paramagnetic or DEAE-cellulose beads) and polystyrene microtitre plates. Particularly preferred are membranes and beads.

In a particularly preferred such aspect of the invention, one or more isozymes of the NADPH-dependent oxidoreductase OYE (EC 1.6.99.1), such as OYE1 (SEQ ID NO:1), OYE2 (SEQ ID NO:2) or OYE3 (SEQ ID NO:3), and one or more cofactors such as NADH or preferably NADPH, are immobilized onto one or more solid supports to produce an enzyme-containing solid support that may be used in the methods described below to produce a fermented malt beverage having enhanced flavor stability. Methods of simultaneously coupling enzymes (crude or purified) and cofactors, while maintaining enzyme activity, are known in the art (see, e.g., Kragl, U., et al., *Biotechnol. Bioeng.* 52:309–319 (1996); Nidetzky, B., et al., *Biotechnol. Bioeng.* 52:387–396 (1996)).

Alternatively, the enzyme-containing solid support may comprise, in addition to the one or more enzyme cofactors, one or more of the genetically modified cells of the invention that produce enhanced amounts of one or more of the flavor-stabilizing reductase enzymes described above. In the case of immobilized cells, the solid phase support is important in terms of providing an adequate environment for cell growth and contact with the aqueous substrate. The cells used in the present methods may be immobilized onto solid supports and cultured according to any means known in the art (see, e.g., U.S. Pat. No. 5,079,011). Furthermore, the use of immobilized growing cells in fermentation and ethanol production has previously been described (for reviews, see Godia, F., et a., *Process. Biochem.* 4:43–48 (1987), and de Gooijer, C. D., et al, *Enz. Microb. Technol.* 18::202–219 (1996)).

The above-described active solid supports, such as the enzyme-containing solid supports, may then be used in methods to stabilize the flavor of a malt beverage. Such methods may comprise, for example, contacting the grain malt, wort mixture (prior to or following fermentation) or fermented malt beverage (prior to or following processing) with one or more of the active solid supports described above, under conditions suitable to stabilize the flavor of the finished fermented malt beverage as described above. In a particularly preferred such method, these active solid supports are used to contact the wort prior to fermentation, the fermented malt beverage prior to processing, or the processed fermented malt beverage prior to packaging. Most preferably, flavor stabilization is achieved by contacting the fermented malt beverage with one or more of the active solid supports prior to packaging the beverage. The invention also provides a fermented malt beverage, such as a beer, produced by these methods.

As noted above, in one particularly preferred aspect of the invention the active solid supports used in these methods may comprise immobilized cells, extracts, digests or purified reductase enzymes. According to the methods of this aspect of the invention, the cells, extracts or digests, or purified reductase enzymes of the invention work in concert with the enzyme cofactors to reduce the off-flavor-producing compounds and precursors in the grain malt, wort or fermented malt beverage as described above. The cofactors are then regenerated in situ on the solid support without further manipulation (see Kragl, U., et al., *Biotechnol. Bioeng.* 52:309–319 (1996); Nidetzky, B., et al., *Biotechnol Bioeng.* 52:387–396 (1996)). Thus, the present methods provide a continuous production system for the enzymatic stabilization of a fermented malt beverage. Furthermore, since the enzymes and cofactors are immobilized on a solid support, the resulting fermented malt beverage having enhanced flavor stability can be considered to be essentially free of processing aids and additives as these compounds are described above.

The optimal amounts of reductase enzymes necessary to stabilize the flavor of the finished malt product were determined using the analytical methods set forth in the Examples below. According to these methods, the optimal concentration ranges for crude or purified reductase enzymes added per se to the grain malt, wort mixture or finished malt beverage are about 5–500 units/ml, preferably about 10–250 units/ml, more preferably about 25–100 units/ml, and most preferably about 50 units/ml. For immobilized enzymes, optimal concentration ranges are about 100 to about 600 units/cm$^2$, about 200 to about 450 units/cm$^2$, or about 250 to about 300 units/cm$^2$; corresponding optimal concentration ranges of cofactors are about 50 to about 450 $\mu$mol/cm$^2$, about 80 to about 250 $\mu$mol/cm$^2$, or about 100 to about 150 $\mu$mol/cm$^2$. As used herein, one unit of enzyme is defined as the amount of enzyme that catalyzes the oxidation of 1 micromole of NADPH per minute at 25° C. It should be noted that while these ranges are described in terms of use of a single reductase enzyme, the methods of the present invention contemplate the addition of one or more additional flavor-stabilizing proteins, including the reductase enzymes described above, simultaneously, sequentially, or by a single injection of two or more pre-blended components.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES

Materials and Methods

The following materials and methods were generally used in the Examples.

Organoleptic Testing

Organoleptic testing is designed to give an indication of the stability of bottled beer, as determined by subjective methods (e.g., "taste testing"). In this approach, filtered, enzyme-treated beer is packaged in standard 275 ml bottles, and samples are subjected to an alternating cooling (0° C. for 24 hours) and heating (40° C. for 24 hours) cycle. The flavor of the beer is then evaluated organoleptically by skilled tasters. A control sample of beer not treated with enzyme is temperature-cycled at the same time to provide a standard. The flavor indices of these treated and untreated beers are then compared to determine the improved stability achieved by treating beer with an oxoaldehyde reductase enzyme. The results of this organoleptic testing are then compared to those obtained by chromatographic measurements of the chemical indices of flavor described below.

Analysis of LC18 and 5-HMF.

Analysis of the chemical indices LC18 and 5-HMF was performed by liquid chromatography, using a Waters HPLC system which consisted of a 600 pump, Wisp 717 autosampler, Millennium 2010 Chromatography Manager v 2.1. Separation was carried out in an Aminex HPX-87H column 300×7.8 mm, 9 $\mu$m held at 55° C. Elution was monitored with a Waters 991 Photodiode Array Detector (200 nm–300 nm) and the quantitation of 5-HMF and LC18 peak was carried out at 283 nm. For analysis, 50 $\mu$l of degassed beer was injected in duplicate samples and eluted with 0.05 M $H_2SO_4$ over 25 min at a flow rate of 1.0 ml/min. Quantitation of 5-HMF was performed using an external calibration curve of the respective pure compounds (Sigma; Saint Louis, Mo.).

Analysis of CE3.

All samples of beer were degassed in an ultrasonic bath before injection and analyzed in duplicate. Analyses were performed on a 270A-HT Applied Biosystems Capillary Electrophoresis System. An untreated fused silica capillary of 50 $\mu$m internal diameter and 72 cm length (50 cm to the detector) was used in all separations. Samples were vacuum-injected for 3.5 seconds, and electrophoretic separations were carried out in 20 mM sodium citrate buffer, pH 2.5, at a voltage of 15 kV for 20 minutes. Detection was performed at 200 nm. Data acquisition and processing was accomplished using a Model 600 Data Analysis System Software (Applied Biosystems) for Macintosh.

Derivatization of Dicarbonylic Compounds with 1,2-phenylenediamine and Determination of Quinoxalines by HPLC A fixed volume (2.2 ml) of 5% 1,2-phenylenediamine (OPD) in methanol was added to a bottle of beer (222 ml) that was then recapped and kept at 20° C. for 12 hours. After 12 hours of reaction, 25 ml of sample were extracted with chloroform (3×8 ml). The chloroform organic phase was removed by centrifugation at 3000 rpm for 10 min, collected, washed with 0.1 M HCl (3×8 ml) in order to remove the unreacted 1,2-phenylenediamine, and semi-dried with magnesium sulfate. The semi-dried organic phase, which contained the hydrophobic quinoxaline derivatives, was then rotavapped to dryness, and the residue resuspended in 250 $\mu$l of acetonitrile, and diluted 1/10 (50% solvent A and 50% solvent B) before chromatographic analysis. Hydrophobic quinoxalines were analyzed using Method I (see below). The aqueous phase, containing hydrophilic quinoxalines, was injected directly and analyzed using Method II (see below).

Figure 6B:
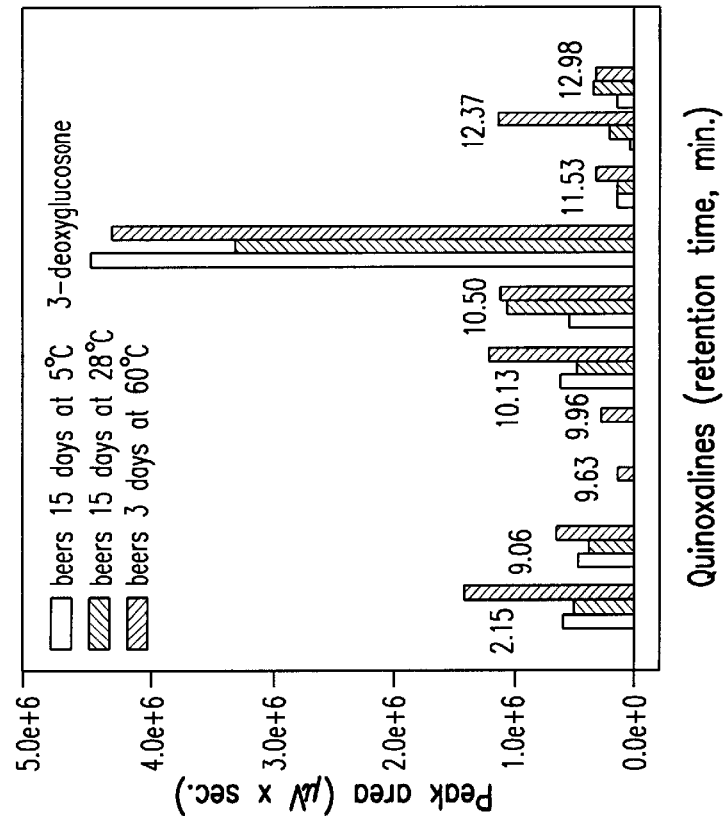
Figure 6A:
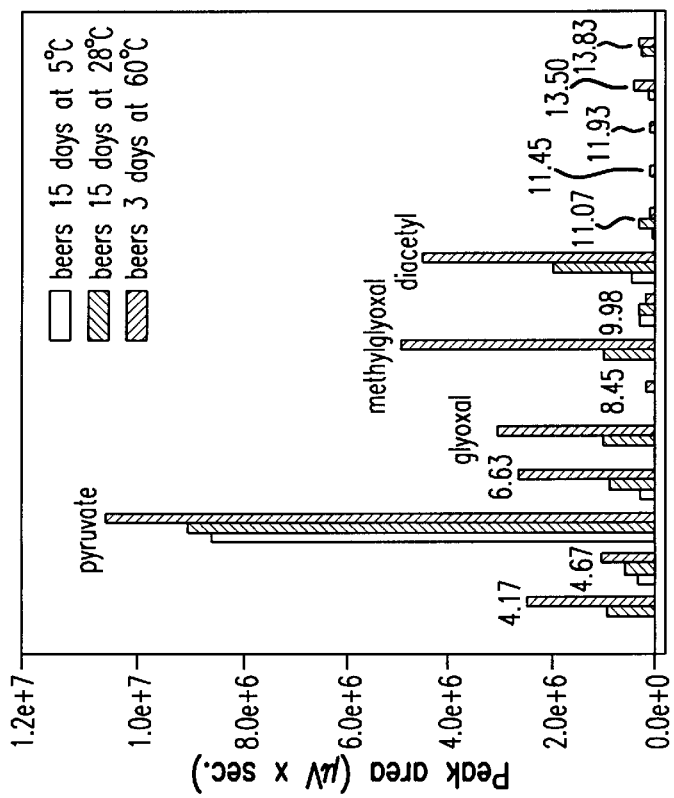

Chromatographic conditions were as follows: a Nova-Pak C18 (Waters) column 3.9×150 mm, 4 $\mu$m was used. The mobile phase was: solvent A—95% water (Milli-Q) and 5% acetonitrile; solvent B—90% acetonitrile and 10% water; flow rate 0.7 ml/min. Elution was monitored with a Waters 991 Photodiode Array Detector (200 nm–360 nm). Typical results are shown in FIGS. 5 and 6.

Methods I and II were as follows:

| | Method I | |
|---|---|---|
| Time (min) | % Solvent A | % Solvent B |
| 0 | 85 | 15 |
| 12 | 60 | 40 |
| 20 | 100 | 0 |

| | Method II | |
|---|---|---|
| Time (min) | % Solvent A | % Solvent B |
| 0 | 100 | 0 |
| 3 | 100 | 0 |
| 10 | 75 | 25 |
| 15 | 75 | 25 |

Example 1

Purification of NADPH-dependent Oxidoreductase from Brewer's Yeast

Brewer's yeast cells for pitching (Polar; Caracas, Venezuela) were washed twice with 25 mM potassium phosphate buffer pH 7.5 (buffer A), suspended in the same buffer and disrupted by glass beads (0.5 mm diameter) in a Disintegrator-S (IMAO) at 3000 rpm for 10 minutes. The cell homogenates were centrifuged at 10,000 g for 40 minutes, and the supernatant (cytosolic fraction) was used for the purification of NADPH-dependent oxidoreductase activities.

The enzymes were purified by successive column chromatographies on a FPLC System (Pharmacia), as summarized in FIG. 7. All the procedures were carried out at 5° C.

The cytosolic fraction was applied to a DEAE-Sepharose column previously equilibrated with buffer A. The column was first washed with the same buffer and then with the buffer A containing 250 mM and 500 mM KCl, and the enzyme activity was eluted as two peaks. The first peak (Reductase 1) was eluted with the washing buffer, and the second (Reductase 2) was eluted with the buffer containing 250 mM KCl. Both fractions were pooled separately and precipitated by the addition of ammonium sulfate. Reductase 1 was precipitated with ammonium sulfate to give 50% saturation, the mixture was stirred for 30 minutes at 5° C. and then centrifuged for 20 minutes at 4360 g. The resulting supernatant was brought up to a saturation of 90% ammonium sulfate, stirred for 30 minutes, and centrifuged for 20 minutes at 4360 g. Reductase 2 was precipitated with ammonium sulfate to give 80% saturation and processed as described above. The pellets obtained after this centrifugation were resuspended, separately, in a minimal amount of 5 mM potassium phosphate pH 6.5 (buffer B) and dialyzed overnight against the same buffer.

The dialyzed enzyme fractions were applied separately on identical CM-Sephadex columns previously equilibrated with buffer B. In both cases, reductase activity did not interact with the resin and the proteins were eluted with the equilibration buffer. Fractions with reductase activity were pooled and concentrated by ultrafiltration with an Amicon YM-10 membrane.

The pooled enzyme fractions were then adsorbed separately to identical Cibacron Blue columns previously equilibrated with 25 mM potassium phosphate pH 7.0 (buffer C). Reductase 1 was eluted with the buffer containing 400 mM KCl, whereas Reductase 2 was eluted with a 0 to 1 M KCl gradient in buffer C.

The fractions showing reductase activity were pooled separately and concentrated to a 2 ml volume as described previously. Reductase 1 was applied to a Red Sepharose column previously equilibrated with buffer C and eluted with a 0 to 1 M KCl linear gradient in buffer C, whereas Reductase 2 was applied to a Superose 12 column equilibrated with the same buffer.

As a last purification step, both enzyme preparations (Reductase 1 and Reductase 2) were subjected to a preparative reverse-phase column. Reductase 1 was applied to a ProRPC column (Pharmacia), whereas Reductase 2 was applied to a Resource RPC 1 ml column (Pharmacia Biotech). Both columns were connected separately to a Waters LC Module I Plus HPLC system. The protein elution was monitored by measuring the absorbance 215 nm, and the protein-containing peaks were collected separately. The purified enzymes were freeze-dried and stored at −70° C.

The activities of the isolated and purified oxoaldehyde reductase enzymes were determined in a mixture containing 9 mM methylglyoxal, 0.1 mM NADPH, 25 mM potassium phosphate buffer (pH 7.0), and the fraction enzyme (8 μg approximately) in a total volume of 0.5 ml. The reaction was monitored at 340 nm. All assays were performed at 25° C. One unit of the enzyme was defined as the amount of enzyme that the catalyzes the oxidation of 1 μmol of NADPH per minute at 25° C.

Example 2

Biochemical Characterization of Reductase 1

Chromatographic fractions from Example 1 which showed enzymatic activity were used for the estimation of molecular weight by both gel filtration chromatography and 12.5% polyacrylamide gel electrophoresis containing sodium dodecylsulfate (SDS-PAGE) as described by Weber and Osborn (*J. Biol. Chem.* 244:4406–4412 (1960)). Protein was determined by the method of Lowry et al. (*J. Biol. Chem.* 193:265–275 (1951)), using bovine serum albumin as standard.

Analytical gel filtration in HPLC was performed on a Sephacryl S-200 column (Waters), which was equilibrated and eluted with buffer C. Both enzymes eluted as single peaks; the molecular weight of native Reductase 1, as determined by this method, was shown to be 86 kDa. However, analysis of Reductase 1 by SDS-PAGE showed a unique band of molecular weight 44 kDa (FIG. 8), whereas a single band of 39.5 kDa was seen for Reductase 2 (FIG. 9).

The polyacrylamide gel containing the Reductase 1 was scanned using a camera (UVP), and the digital image was evaluated by a computer program (GelWorks, UVP). This densitometric analysis showed that Reductase 1 was purified to near homogeneity (96%) as a unique band of the appropriate molecular weight.

The purified Reductase 1 enzyme was partially sequenced by the Edman degradation method (Edman, P., *Acta Chem. Scan.* 4:483 (1950)) using a ProSequencer MilliGen/Biosearch instrument, the amino acid derivatives being identified on line after each cycle of degradation. The first 30 amino acid residues of this purified Reductase 1 were found to be as follows: MPFVKDFKPQALGDTNLFKPIKIGN-NELLH (SEQ ID NO:4).

Example 3

Identification and Cloning of the Oxidoreductase OYE2from Brewer's Yeast

The identification of the yeast Reductase 1 was achieved by its biochemical purification from brewing yeast as in Example 1 and by its N-terminal amino acid sequencing as in Example 2. The first 30 amino acid residues of the protein (SEQ ID NO:4) revealed it to be related to a well-known reductase called Old Yellow Enzyme (OYE; EC 1.6.99.1) (Warburg, O., and Christian, W., *Biochem. Z.* 266:377–411 (1933)). This enzyme was first characterized from the brewer's yeast *Saccharomyces carlsbergenesis,* having an apparent molecular weight of 45 kDa in SDS-PAGE and enzymatic activity characteristic of an NADPH-dependent oxidoreductase. The corresponding genes for three separate OYE isozymes, OYE1, OYE2 and OYE3, were later cloned, sequenced and expressed in *E coli,* and complete amino acid sequences for each were reported (OYE1: SEQ ID NO:1, Saito, K., et al., *J. Biol. Chem.* 266:20720–20724 (1991); OYE2: SEQ ID NO:2, Stott, K., et al., *J. Biol. Chem.* 268:6097–6106 (1993); OYE3: SEQ ID NO:3, Niino, Y. S., et al., *J. Biol. Chem.* 270:1983–1991 (1995)).

In the present studies, Reductase 1 was identified by comparing the sequence of the first 30 amino acid residues of the protein against the Saccharomyces Genome Database, SGD, via the World Wide Web (Cherry, J., et al., Saccharomyces Genome Database, which is available via Internet at http:\\genome-www.stanford.edu\ Saccharomyces). This sequence comparison unambiguously showed Reductase 1 to have 100% homology to OYE2, 91% homology to OYE1 and 81% homology to OYE3, all enzymes isolated from the yeast genus Saccharomyces.

The DNA sequence of the OYE2 gene from *Saccharomyces cerevisiae* was retrieved from the SGD (GenBank Accession No. L06124), and after a DNA sequence analysis two primers were designed that were capable of specifically amplifying the gene from the brewing yeast genome via PCR. The PCR primers (Forward primer: 5'-GGA ATT CAT GCC ATT TGT TAA GGA C-3' (SEQ ID NO:5); Reverse primer: 5'-CTC TAG ATT AGA GCT TCT TCG TAC G-3' (SEQ ID NO:6)) additionally comprised the recognition sequence sites for EcoRI (5' termini) and XbaI (3' termini), such that the PCR products were synthesized with terminal EcoRI and XbaI restriction sites. These restriction sites permitted the cloning of the OYE2 gene in frame into pProEx-HTa (Life Technologies, Inc.; Rockville, Md.).

After restriction enzyme characterization, the amplified gene of OYE2 was subcloned into the expression vector pProEx-HTa to form plasmid pProEx-OYE2. *E. coli* host cells (XLI-blue, JM109 or DH5α strains) were then transformed with this plasmid.

Recombinant bacteria were screened in LB agar plates containing 100 μg/ml ampicillin, and the ampicillin-resistant bacteria were further tested by isolating their plasmids using well-known methods (Sambrook, J., et al., *Molecular Cloning: A Laboratory Manual*, 2nd Ed., Cold Spring Harbor, N.Y.: Cold Spring Harbor Laboratory (1989)). The positive recombinant bacteria carrying the pProEx-OYE2 plasmid were induced with 600 μM IPTG for 3 hours to express the expected fusion polypeptide of 52 kDa. The recombinant protein represented about 18% of total bacterial proteins and was further purified by affinity chromatography according to the manufacturer's recommendations for the pProEx expression system.

Example 4

Substrate Specificity Assays

Various carbonyl compounds were assayed as substrates for the isolated and purified reductase enzymes. As shown in FIG. 10, both Reductase 1 and Reductase 2 acted on 2-oxoaldehydes such as methylglyoxal and 3-deoxyglucosone. Reductase 1 showed a higher activity than Reductase 2 on compounds with a single keto or aldo group such as acetaldehyde and pyridine-3-aldehyde. Glucuronate was found to be a better substrate for Reductase 2 than for Reductase 1, whereas metyrapone was an acceptable substrate for both enzymes. Both reductases showed little or no effect on the assayed aldoses (glucose, galactose and xylose). It is noteworthy that neither enzyme showed any appreciable activity on pyruvate.

These results demonstrate that Reductase 1 and Reductase 2 are chemically and kinetically distinguishable.

Example 5

Effect of the Reductases on LC18

In order to determine the effect of both reductases on the intensity of the LC18 peak, a 1 ml mixture of fresh beer, 25 mM potassium phosphate buffer (pH 7.0), 0.1 mM NADPH and the required volume of enzyme to obtain a final concentration in the solution of 50 units/ml of enzyme was incubated at 25° C. for 30 minutes. After the incubation, the treated beer was analyzed on an Aminex HPX-87H column connected to a Waters HPLC System under the conditions described above.

As demonstrated in FIG. 11, treatment of beer with Reductase 1 or Reductase 2 caused a significant decrease in the area of the LC18 peak (arrows), relative to that in an untreated control beer. Treatment of beer with Reductase 1 induced a larger decrease in the LC18 peak than did treatment with Reductase 2, perhaps reflecting the higher specific activity of the former for various single keto- and single aldo-carbonyl substrates as shown in FIG. 10. These results demonstrate that treatment with either Reductase 1 or Reductase 2, and preferably with Reductase 1, can reduce the formation of stale flavor indices such as LC18 in fresh beer.

Example 6

Flavor Evaluation

For sensory evaluations of beer flavor, we used a panel of six trained tasters. Each participant was asked to compare flavor profiles and determine the presence or absence of flavor components, associated with freshness degree of beer in the following samples: 1) fresh beer at 5° C.; 2) control beer at 28° C.; and 3) beer with added Reductase 1 at 28° C. The scale used to report the freshness degree of beer was from "1" to "5" (with "5" indicating the freshest taste).

Beers were prepared as follows:

1) Control beers: 10 ml of beer were taken out of each six bottles of 222 ml of pasteurized, fresh beer under a $CO_2$ current. This volume was replaced with 6 ml of buffer C and 4 ml of 3 mM NADPH, and the bottles were then recapped. Three bottles were stored at 5° C. for 15 days and the other three at 28° C. for 15 days.

2) Experimental beers: 10 ml of beer were taken out of each of three bottles of 222 ml of pasteurized, fresh beer under a $CO_2$ current, and this volume was replaced with 5.4 ml of buffer A, 4 ml of 3 mM NADPH and 0.6 ml of Reductase 1. The bottles were recapped and stored at 28° C. for 15 days.

The fresh, control and experimental beers were then subjected to evaluation by the panel of tasters. As shown in FIG. 12, these flavor evaluation tests demonstrated a significant increase in freshness degree in beers containing reductase 1, compared with control beers at 28° C. Together with those for chromatographic testing above, these results indicate that treatment of beer with Reductase 1 stabilizes the flavor of the beer.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of stabilizing the flavor of a fermented malt beverage comprising contacting said beverage with a flavor-stabilizing amount of one or more reductase enzymes having an amino acid sequence selected from the group consisting of SEQ ID NO:1 SEQ ID NO:2 and SEQ ID NO:3.

2. A method of producing a processed fermented malt beverage, said method comprising:
   (a) producing a grain malt;
   (b) producing a wort from said grain malt;
   (c) fermenting said wort to produce a fermented malt beverage;
   (d) processing said fermented malt beverage to produce a processed fermented malt beverage; and
   (e) packaging said processed fermented malt beverage, wherein a flavor-stabilizing amount of one or more reductase enzymes having an amino acid sequence selected from the group consisting of SEQ ID NO:1, SEQ ID NO:2 and SEQ ID NO:3 is added to one or more of: said malt produced in (a), said wort produced in (b), said fermented malt beverage produced in (c), said processed fermented malt beverage produced in (d), and said packaged beverage produced in (e).

3. The method of claim 2, wherein said reductase enzyme is added to said wort prior to said fermentation step.

4. The method of claim 2, wherein said reductase enzyme is added to said fermented malt beverage prior to said processing step.

5. The method of claim 2, wherein said reductase enzyme is added to said processed fermented malt beverage prior to said packaging step.

6. The method of claim 1 or claim 2, wherein said reductase enzyme is immobilized on a solid support.

7. The method of claim 6, wherein said solid support further comprises NADPH.

8. The method of claim 1 or claim 2, wherein said reductase enzyme is purified.

9. The method of claim 1 or claim 2, wherein said fermented malt beverage is beer.

10. The method of claim 1 or claim 2, wherein said reductase enzyme is isolated from a yeast cell.

11. The method of claim 10, wherein said yeast cell is a Saccharomyces spp. cell.

12. The method of claim 11, wherein said yeast cell is a *Saccharomyces cerevisiae* cell or a *Saccharomyces carlsbergensis* cell.

13. The method of claim 10, wherein said yeast cell has been genetically modified to permit the enhanced production of one or more of said reductase enzymes relative to the production in an unmodified yeast cell.

14. A method of producing a fermented malt beverage having a stabilized flavor, said method comprising:
   (a) producing a grain malt;
   (b) producing a wort from said grain malt; and
   (c) fermenting said wort to produce a fermented malt beverage having stabilized flavor,
wherein a flavor-stabilizing amount of one or more reductase enzymes having an amino acid sequence selected from the group consisting of SEQ ID NO:1, SEQ ID NO:2 and SEQ ID NO:3 is added to one or more of: said malt produced in (a), said wort produced in (b), and said fermented malt beverage produced in (c).

15. A method of producing a fermented malt beverage having stabilized flavor, said method comprising
   (a) producing a grain malt;
   (b) producing a wort from said grain malt;
   (c) contacting said wort with a genetically modified Saccharomyces spp. cell secreting enhanced amounts of one or more reductase enzymes, relative to the amounts of said reductase enzymes secreted in the wild-type strain of said cell, wherein said one or more reductase enzymes have an amino acid sequence selected from the group consisting of SEQ ID NO:1, SEQ ID NO:2 and SEQ ID NO:3; and
   (d) allowing said cell to ferment said wort, thereby producing a fermented malt beverage having stabilized flavor.

16. The method of claim 14 or claim 15, wherein said reductase enzyme has the amino acid sequence set forth in SEQ ID NO:1.

17. The method of claim 14 or claim 15, wherein said reductase enzyme has the amino acid sequence set forth in SEQ ID NO:2.

18. The method of claim 14 or claim 15, wherein said reductase enzyme has the amino acid sequence set forth in SEQ ID NO:3.

19. The method of claim 14, wherein said cell is a *Saccharomyces cerevisiae* or a *Saccharomyces carlsbergensis* cell.

20. The method of claim 14 or claim 15, wherein said fermented malt beverage is a beer.

* * * * *

SEQUENCE LISTING

<160> NUMBER OF SEQ ID NOS: 6

<210> SEQ ID NO 1
<211> LENGTH: 400
<212> TYPE: PRT
<213> ORGANISM: Saccharomyces carlsbergensis

<400> SEQUENCE: 1

```
Met Ser Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Leu His Pro Gly Asn Ile
        35                  40                  45

Pro Asn Arg Asp Trp Ala Val Glu Tyr Tyr Thr Gln Arg Ala Gln Arg
    50                  55                  60

Pro Gly Thr Met Ile Ile Thr Glu Gly Ala Phe Ile Ser Pro Gln Ala
65                  70                  75                  80

Gly Gly Tyr Asp Asn Ala Pro Gly Val Trp Ser Glu Gln Met Val
                85                  90                  95

Glu Trp Thr Lys Ile Phe Asn Ala Ile His Glu Lys Lys Ser Phe Val
            100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Phe Met
        130                 135                 140

Asp Ala Glu Gln Glu Ala Lys Ala Lys Ala Asn Asn Pro Gln His
145                 150                 155                 160

Ser Leu Thr Lys Asp Glu Ile Lys Gln Tyr Ile Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Thr Arg Thr Asp Glu Tyr Gly Gly Ser Ile Glu Asn Arg Ala Arg Phe
    210                 215                 220

Thr Leu Glu Val Val Asp Ala Leu Val Glu Ala Ile Gly His Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Ala Gly Glu
            260                 265                 270

Leu Glu Lys Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Glu Gly Gly Ser Asn Asp Phe Val Tyr Ser Ile Trp Lys Gly Pro
305                 310                 315                 320

Val Ile Arg Ala Gly Asn Phe Ala Leu His Pro Glu Val Val Arg Glu
                325                 330                 335

Glu Val Lys Asp Lys Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
```

-continued

```
                355                 360                 365
Lys Tyr Asp Arg Asp Thr Phe Tyr Gln Met Ser Ala Trp Gly Tyr Ile
        370                 375                 380

Asp Tyr Pro Thr Tyr Glu Glu Ala Leu Lys Leu Gly Trp Asp Lys Lys
385                 390                 395                 400

<210> SEQ ID NO 2
<211> LENGTH: 400
<212> TYPE: PRT
<213> ORGANISM: Saccharomyces carlsbergensis

<400> SEQUENCE: 2

Met Pro Phe Val Lys Asp Phe Lys Pro Gln Ala Leu Gly Asp Thr Asn
  1               5                  10                  15

Leu Phe Lys Pro Ile Lys Ile Gly Asn Asn Glu Leu Leu His Arg Ala
                 20                  25                  30

Val Ile Pro Pro Leu Thr Arg Met Arg Ala Gln His Pro Gly Asn Ile
             35                  40                  45

Pro Asn Arg Asp Trp Ala Val Glu Tyr Tyr Ala Gln Arg Ala Gln Arg
         50                  55                  60

Pro Gly Thr Leu Ile Ile Thr Glu Gly Thr Phe Pro Ser Pro Gln Ser
 65                  70                  75                  80

Gly Gly Tyr Asp Asn Ala Pro Gly Ile Trp Ser Glu Gln Ile Lys
                 85                  90                  95

Glu Trp Thr Lys Ile Phe Lys Ala Ile His Glu Asn Lys Ser Phe Ala
                100                 105                 110

Trp Val Gln Leu Trp Val Leu Gly Trp Ala Ala Phe Pro Asp Thr Leu
            115                 120                 125

Ala Arg Asp Gly Leu Arg Tyr Asp Ser Ala Ser Asp Asn Val Tyr Met
        130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335
```

```
Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
            355                 360                 365

Lys Tyr Asp Arg Asp Thr Phe Tyr Lys Met Ser Ala Glu Gly Tyr Ile
            370                 375                 380

Asp Tyr Pro Thr Tyr Glu Glu Ala Leu Lys Leu Gly Trp Asp Lys Asn
385                 390                 395                 400

<210> SEQ ID NO 3
<211> LENGTH: 400
<212> TYPE: PRT
<213> ORGANISM: Saccharomyces carlsbergensis

<400> SEQUENCE: 3

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
            35                  40                  45

Pro Asn Lys Glu Trp Ala Ala Val Tyr Tyr Gly Gln Arg Ala Gln Arg
            50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Ser Leu Gly Trp Ala Ser Phe Pro Asp Val Leu
            115                 120                 125

Ala Arg Asp Gly Leu Arg Tyr Asp Cys Ala Ser Asp Arg Val Tyr Met
            130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Asp Tyr Ile His
            165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
            195                 200                 205

Lys Arg Thr Asp Glu Tyr Gly Gly Thr Ile Glu Asn Arg Ala Arg Phe
            210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
            245                 250                 255

Gly Ala Glu Pro Gly Ile Ile Ala Gln Tyr Ser Tyr Val Leu Gly Glu
            260                 265                 270

Leu Glu Lys Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
            290                 295                 300

Tyr Ser Glu Gly Thr Asn Asp Phe Ala Tyr Ser Ile Trp Lys Gly Pro
305                 310                 315                 320
```

```
Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400

<210> SEQ ID NO 4
<211> LENGTH: 30
<212> TYPE: PRT
<213> ORGANISM: Saccharomyces carlsbergensis

<400> SEQUENCE: 4

Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His
            20                  25                  30

<210> SEQ ID NO 5
<211> LENGTH: 25
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 5
ggaattcatg ccatttgtta aggac                                            25

<210> SEQ ID NO 6
<211> LENGTH: 25
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 6
ctctagatta gagcttcttc gtacg                                            25
```